United States Patent
Tutera

(10) Patent No.: US 11,798,659 B2
(45) Date of Patent: *Oct. 24, 2023

(54) SYSTEM AND METHOD FOR AUTOMATED DOSAGE CALCULATION AND PATIENT TREATMENT LIFE CYCLE

(71) Applicant: The SottoPelle Group, LLC, Scottsdale, AZ (US)

(72) Inventor: Gino Tutera, Scottsdale, AZ (US)

(73) Assignee: The Sotto Pelle Group, LLC, Scottsdale, AZ (US)

( * ) Notice: Subject to any disclaimer, the term of this patent is extended or adjusted under 35 U.S.C. 154(b) by 500 days.

This patent is subject to a terminal disclaimer.

(21) Appl. No.: 16/799,820

(22) Filed: Feb. 24, 2020

(65) Prior Publication Data
US 2020/0219600 A1 Jul. 9, 2020

Related U.S. Application Data

(63) Continuation of application No. 15/125,529, filed on Sep. 12, 2016, now Pat. No. 10,572,628.

(60) Provisional application No. 61/951,415, filed on Mar. 11, 2014.

(51) Int. Cl.
| | |
|---|---|
| *G16H 10/60* | (2018.01) |
| *G16H 10/20* | (2018.01) |
| *G16H 40/20* | (2018.01) |
| *G16H 50/20* | (2018.01) |
| *G16H 20/10* | (2018.01) |
| *G06Q 10/00* | (2023.01) |
| *G16H 50/70* | (2018.01) |
| *G16H 40/67* | (2018.01) |

(52) U.S. Cl.
CPC .............. *G16H 10/20* (2018.01); *G06Q 10/00* (2013.01); *G16H 10/60* (2018.01); *G16H 20/10* (2018.01); *G16H 40/20* (2018.01); *G16H 50/20* (2018.01); *G16H 40/67* (2018.01); *G16H 50/70* (2018.01)

(58) Field of Classification Search
CPC ......... G16H 40/20; G16H 50/20; G16H 10/20
See application file for complete search history.

(56) References Cited

U.S. PATENT DOCUMENTS

| | | | | |
|---|---|---|---|---|
| 2007/0259348 A1* | 11/2007 | Phadke | ................ | C12Q 1/6806 435/6.12 |
| 2011/0066450 A1* | 3/2011 | Karapanos | ............. | A61B 5/145 705/3 |

OTHER PUBLICATIONS

Mason. Innovative Diagnostic and Treatment Options. Alternative and Complementary Therapies. Aug. 2007 vol. 13, No. 4. pp. 211-216. Especially p. 215, col. 2, Para 2-3 (Year: 2007).*

(Continued)

*Primary Examiner* — Michael Tomaszewski
*Assistant Examiner* — Mohmad Muqueeth
(74) *Attorney, Agent, or Firm* — Michelle L. Gross, P.C.

(57) ABSTRACT

A system and method for automatically calculating an accurate recommended dosage for hormone replacement therapy and automating the life cycle of a patient's treatment over time. The system and method can automatically acquire relevant patient parameters and apply a consistent formulaic approach to help reduce incorrect dosage determinations. A pellet insertion size may be determined and documented based on a calculated dosage, and an insertion side and lot numbers may be tracked and managed. In addition, corresponding revenues may be tracked and profitability may be reported for hormone replacement therapy practices.

16 Claims, 32 Drawing Sheets

(56) References Cited

OTHER PUBLICATIONS

Nelson. Implementing Metrics Management for Improving Clinical Trials Performance [online] May 10, 2013 [retrieved Jan. 18, 2019], Available on the internet: <https://web.archive.org/web/20130510020333/http://www.b-eye-network.com/view/7981> (Year: 2013).*

* cited by examiner

FIG. 14

Prescribe Patient

| Estradiol (mg) | | | | | | | | |
|---|---|---|---|---|---|---|---|---|
| + 6 − | + 10 − | + 12.5 − | + 15 − | + 19 − | + 20 − | + 22 − | + 25 − | Total |
| | | | 1 | | | | 3 | 90 |

| Testosterone (mg) | | | | | | |
|---|---|---|---|---|---|---|
| + 25 − | + 37.5 − | + 50 − | + 87.5 − | + 100 − | + 200 − | Total |
| 1 | | | | | | 25 |

Lot Numbers:

Please enter the following lot numbers

| | | |
|---|---|---|
| Testosterone 25: ( # 1) | AA9812334 | |
| Estradiol 15: ( # 1) | ZY1278364 | |
| Estradiol 25: ( # 1) | BT9811684 | |
| Estradiol 25: ( # 2) | BT9811684 | ⓒ COPY |
| Estradiol 25: ( # 3) | BT9811684 | ⓒ COPY |

— 1501

— 1502

Insertion Note:

Once upon a time, a very long time ago now, about last Friday, Winnie-the-Pooh lived in a forest all by himself under the name of Sanders. ("What does 'under the name' mean?" asked Christopher Robin. "It means he had the name over the door in gold letters, and lived under it." "Winnie-the-Pooh wasn't quite sure," said Christopher Robin.

Save

| Provider | Count | Info Periods | Extra Periods | Extra Periods Sum | Price per Period | Sold |
|---|---|---|---|---|---|---|
| Dr. Lightspoke | 92 | 59 | 53 | $225.00 | $5,004.00 | Yes |
| Gina Tutera MD | 25 | 8 | 17 | $0.00 | $1,189.00 | No |
| Julie Litman | 1 | 1 | 0 | $0.00 | $84.00 | No |
| Mr. Lightspoke | 10 | 9 | 1 | $0.00 | $750.00 | No |
| Steve Nunn | 2 | 0 | 2 | $0.00 | $72.00 | No |
| | 130 | 97 | 73 | $225.00 | $7,086.00 | |

SYSTEM AND METHOD FOR AUTOMATED DOSAGE CALCULATION AND PATIENT TREATMENT LIFE CYCLE

CROSS-REFERENCE TO RELATED APPLICATIONS

This application is a continuation of U.S. application Ser. No. 15/125,529 filed Mar. 11, 2015 and issued on Feb. 25, 2020 as U.S. Pat. No. 10,572,628 entitled "SYSTEM AND METHOD FOR AUTOMATED DOSAGE CALCULATION AND PATIENT TREATMENT LIFE CYCLE" which claims priority to U.S. Provisional Patent Application Ser. No. 61/951,415 filed on Mar. 11, 2014, and entitled "SYSTEM AND METHOD FOR AUTOMATED DOSAGE CALCULATION AND PATIENT TREATMENT LIFE CYCLE."

STATEMENT REGARDING FEDERALLY SPONSORED RESEARCH

N/A

BACKGROUND OF THE INVENTION

The present invention relates to systems and methods for providing a treatment to a patient, for example, providing and monitoring hormone replacement therapy. More particularly, the invention relates to systems and methods for automating a patient treatment lifecycle and a recommended dosage for the patient with respect to hormone replacement therapy.

Hormone replacement therapy includes estradiol and testosterone for females and testosterone for males. Data supports that hormone replacement therapy with pellet implants is more effective and a more bio-identical method to deliver hormones in both men and women. Not only do pellet implants deliver a biologically identical hormone, the pellet implants deliver the hormones in the proper human ratio. Pellet implants are made up of either estradiol or testosterone and are placed under the skin to deliver consistent, healthy levels of hormones for 3-5 months in women and 4-6 months in men. Pellet implants deliver hormones directly into the blood stream, and the release of hormones from pellets is dependent on heart rate and cardiac output (i.e., the rate of hormone release is controlled through the action of the cardiovascular system). Thus, pellet implants result in hormone delivery that nearly approximates what the human gonad can do. In addition, pellet implants can inhibit the fluctuations, or ups and downs, of hormone levels seen with other conventional methods of hormone delivery.

Estrogen delivered by subcutaneous pellets, maintains the normal ratio of estradiol to estrone. This is important for optimal health and disease prevention. Pellets do not increase the risk of blood clots like conventional or synthetic hormone replacement therapy. In both men and women, testosterone has been shown to increase energy, relieve depression, increase sense of well being, relieve anxiety, and improve memory and concentration. Testosterone, delivered by pellet implant, increases lean body mass (muscle strength, bone density) and decreases fat mass. Men and women need adequate levels of testosterone for optimal mental and physical health and for the prevention of chronic illnesses like Alzheimer's and Parkinson's disease and heart attacks, which are associated with low testosterone levels.

The insertion of pellets is a relatively painless procedure done under local anesthesia. The pellets are usually inserted in the lower abdominal wall or upper buttocks through a small incision, which is then taped closed. The experience of the health care professional matters a great deal, not only in placing the pellets, but also in determining the correct dosage of hormones to be used.

Traditionally, determination of recommended dosage for hormone replacement therapy requires that a physician consider numerous factors, including patient age, weight, height, health conditions, contraindications, hormonal levels, previous and current medications, and the like. In all, a proper determination involves correct consideration and weighing of many factors, some of which the physician may not even have easy access to, such as a patient's detailed health record.

However, even if the patient's detailed health record is accessible, many hormone replacement therapy practices require the physician to re-enter data related to the patient to track and/or calculate the proper dosage. This is time consuming and often results in erroneous data entered into input fields of a dosage monitoring system.

SUMMARY OF THE INVENTION

The present invention overcomes the aforementioned drawbacks by providing a system and method that automatically calculates an accurate recommended dosage for hormone replacement therapy and automates the life cycle of the patient's treatment over time. In particular, the present invention can automatically acquire relevant patient parameters and apply a consistent formulaic approach to minimize incorrect dosage determinations, optimize and document a pellet insertion size given the calculated dosage, and track and manage insertion side and lot numbers. In addition, the present invention can track revenues generated and report profitability for hormone replacement therapy practices.

In accordance with one aspect of the invention, a method for providing a dosage on a device including an electronic circuit, an input device, and a display screen is provided. The method includes receiving, from the input device, an input signal of a user indicating an input directed to a patient sex and patient status. The patient status is automatically determined from a group including new patient, returning patient, and booster patient based on the input. If the patient sex is female, the electronic circuit determines an effective estradiol dosage and an effective testosterone dosage using dosage calculation methods selected based on the patient status, automated female input parameters, and female tracking parameters. If the patient sex is male, the electronic circuit determines an effective testosterone dosage using dosage calculation methods selected based on the patient status, automated male input parameters, and male tracking parameters. The determined effective dosages are then displayed on the display screen.

The automated male and female input parameters may include patient physical activity level, number of patient visits, patient age, height, weight, race, number of pregnancies, number of live births, number of abortions, history of renal disease, active liver disease, history of hysterectomy, history of cervical cancer, history of ovarian cancer, history of fibrocystic breast disease, history of breast cancer, current follicle stimulating hormone (FSH) level, current testosterone level, current estradiol level, current non-pellet estradiol dose, history of acne or facial hair, history of hair loss, history of polycystic ovary syndrome (PCOS), history of heavy menses, and history of metabolic syndrome.

The female and male tracking parameters include pellet insertion location, pellet insertion side, pellet dose, pellet lot numbers, insertion notes, previous testosterone dose, and previous estradiol dose. Based on the patient status, automated female and male input parameters, and female and male tracking parameters, the determined effective dosages are calculated and displayed on the display screen. The electronic circuit also determines an estradiol pellet size insertion corresponding to the effective estradiol dosage and a testosterone pellet size insertion corresponding to the effective testosterone dosage using a pellet allocation algorithm. In addition, the electronic circuit also tracks and reports a profitability metric for the patient and provides access to news articles, research articles and videos related to hormone replacement therapy.

In accordance with another aspect of the invention, a system for determining a dosage of a hormone to be administered to a patient is provided. The system includes an input device, a display screen, and at least one electronic circuit. The electronic circuit is configured to receive, from the input device, an input signal of a user indicating an input directed to a patient sex and patient status. The patient status is automatically determined by the electronic circuit from a group including new patient, returning patient, and booster patient based on the input. If the patient sex is female, the electronic circuit determines an effective estradiol dosage and an effective testosterone dosage using dosage calculation methods selected based on the patient status, automated female input parameters, and female tracking parameters. If the patient sex is male, the electronic circuit determines an effective testosterone dosage using dosage calculation methods selected based on the patient status, automated male input parameters, and male tracking parameters. The determined effective dosages are then displayed on the display screen.

The automated male and female input parameters may include patient physical activity level, number of patient visits, patient age, height, weight, race, number of pregnancies, number of live births, number of abortions, history of renal disease, active liver disease, history of hysterectomy, history of cervical cancer, history of ovarian cancer, history of fibrocystic breast disease, history of breast cancer, current follicle stimulating hormone (FSH) level, current testosterone level, current estradiol level, current non-pellet estradiol dose, history of acne or facial hair, history of hair loss, history of polycystic ovary syndrome (PCOS), history of heavy menses, and history of metabolic syndrome.

The female and male tracking parameters include pellet insertion location, pellet insertion side, pellet dose, pellet lot numbers, insertion notes, previous testosterone dose, and previous estradiol dose. Based on the patient status, automated female and male input parameters, and female and male tracking parameters, the determined effective dosages are calculated and displayed on the display screen. The electronic circuit also determines an estradiol pellet size insertion corresponding to the effective estradiol dosage and a testosterone pellet size insertion corresponding to the effective testosterone dosage using a pellet allocation algorithm. In addition, the electronic circuit also tracks and reports a profitability metric for the patient and provides access to news articles, research articles and videos related to hormone replacement therapy.

In accordance with another aspect of the invention a computer-implemented method of providing a dosage and a patient treatment life-cycle on a device comprising an electronic circuit, an input device, and a display screen is provided. The method includes receiving, using the device, an input signal of a user indicating an input directed to a patient sex and a patient status. The patient status is automatically determined by the electronic circuit and includes at least one of a new patient, a returning patient and a booster patient. The electronic circuit determines at least one of an effective estradiol dosage and an effective testosterone dosage using calculation methods selected based on the patient status, automated input parameters, and tracking parameters. A pellet allocation algorithm, stored on the electronic circuit, is applied to determine an estradiol pellet size insertion corresponding to the effective estradiol dosage. A testosterone pellet size insertion is also determined corresponding to the effective testosterone dosage. A quantity of the estradiol pellet size insertion and the testosterone pellet size insertion are minimized. The determined effective dosages, the estradiol pellet size, and the testosterone pellet size are displayed on the display screen.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 14 is an exemplary screen shot of a patient information dialog screen including the patient's insertion history displayed on the user interface of the communication device.

FIG. 15 is an exemplary screen shot of the prescribe patient dialog screen of FIG. 13 showing lot numbers of pellets inserted into the patient.

FIG. 17 is an exemplary screen shot of a patient consult request form to be filled with information about the patient.

FIG. 18 is an exemplary screen shot of a patient consults screen showing a list of consult requests awaiting response from the user.

FIG. 19 is an exemplary screen shot of an individual patient consult screen after selecting the patient consult request from the list of consult requests of FIG. 18.

FIG. 22 is an exemplary screen shot of a news videos and updates screen showing links to news videos and updates related to hormone replacement therapy.

FIG. 24 is an exemplary screen shot of a products screen showing available products for the patient to purchase.

FIG. 26 is an exemplary screen shot of a daily pellet list for entering financial information related to a patient visit.

FIG. 27 is an exemplary screen shot of a patient bill widow showing checkout amounts to be attached to the patient visit of FIG. 26.

FIG. 28 is an exemplary screen shot of an end of day report screen showing a full financial view of a hormone replacement therapy practice.

FIG. 29 is an exemplary screen shot of a prescription summary report screen showing patient and gender counts and revenues and dosing fees per provider.

FIG. 31 is an exemplary screen shot of a provider screen providing a provider record to specify an office.

FIG. 32 is an exemplary screen shot of an assistant login screen that is linked to a provider.

DETAILED DESCRIPTION OF THE INVENTION

Figure 1:
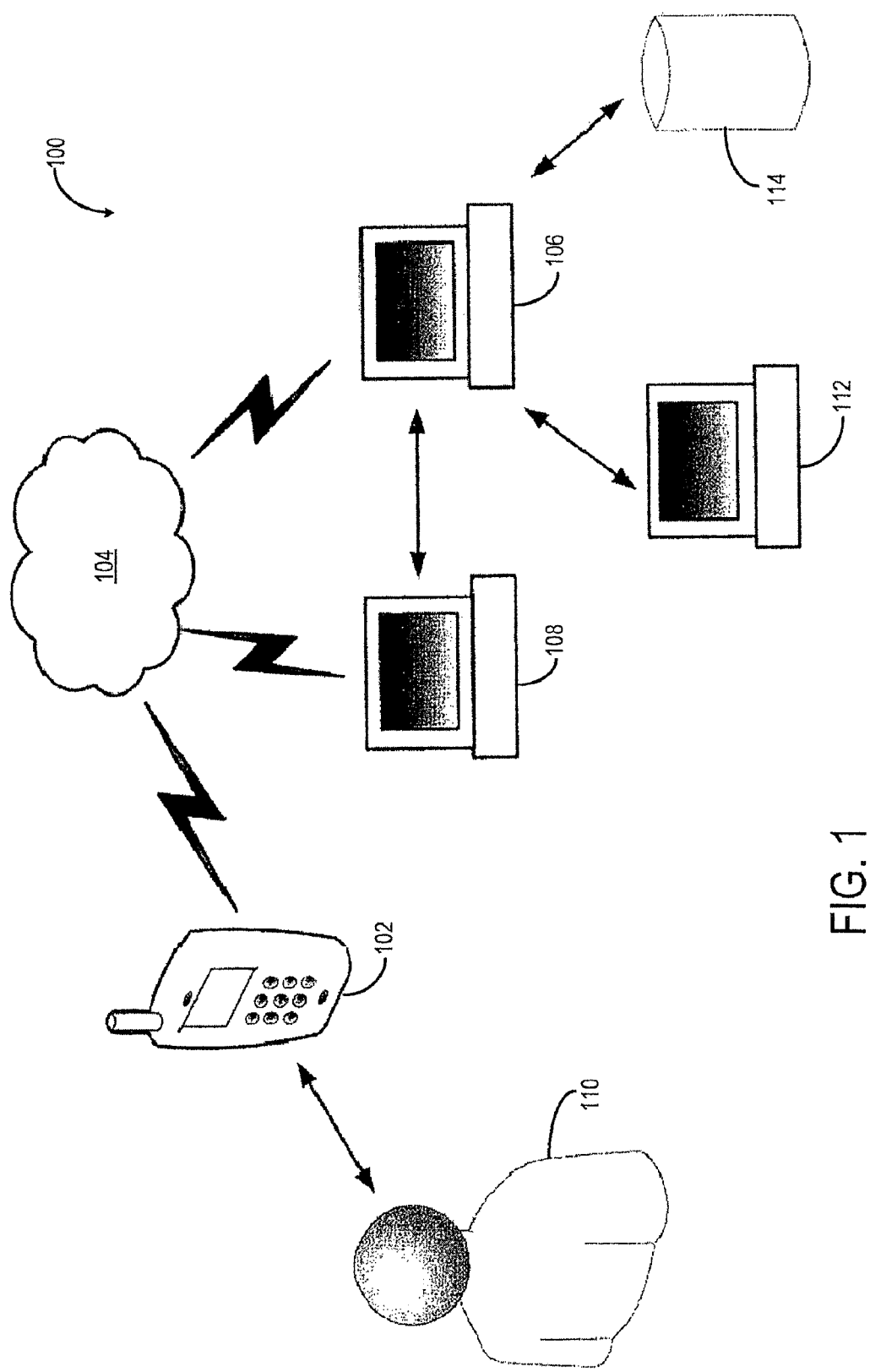
FIG. 1 is a schematic system diagram of an exemplary system configured to implement the present invention.

Referring now to FIG. 1, a system 100, such as a dosage monitoring system, is shown that is configured to determine a recommended dosage for hormone replacement therapy and automate the life cycle of the patient's treatment over time. The system 100 may include, but is not limited to, a communication device 102, a network 104, a user interface (UI) presentation server 108, an application server 106, a cache server 112, and a database 114. Also depicted is a physician user 110, for illustrative purposes. In one exemplary embodiment, the functionality of the UI presentation server 108, application server 106, and cache server 112 may be combined into one or two servers without affecting the efficacy of the system 100. Also, servers 106, 108 and 112 may include identical components or may differ in composition, and are described generically herein as "server 106, 108, 112".

The UI presentation server 108 may provide the user interface to the communication device 102 over the network 104. The network 104 may be a local or wide, wired or wireless, network including, for example, the Internet. Data input through the communication device 102 may be forwarded to the application server 106 for processing and/or storage in the database 114. The database 114 may be accessible by the server 106, 108, 112 and may store data regarding the patient, patient test results, prior dosing information, prior side effects, and any other medically significant information. The server 106, 108, 112 may access the database 114 for information and may also store information therein. The cache server 112 may save frequently-used data for fast access as needed. The database 114 may be a stand-alone database server, a persistent drive, and operating software associated with the application server 106, a cloud-computing database "cloud", or may be implemented by other means. The communication device 102 is configured to communicate with the UI presentation server 108 over the network 104 to send and obtain data regarding a patient. The patient data can include, but is not limited to, information needed for enabling the determination of recommended dosages for hormone replacement therapy.

Figure 2:
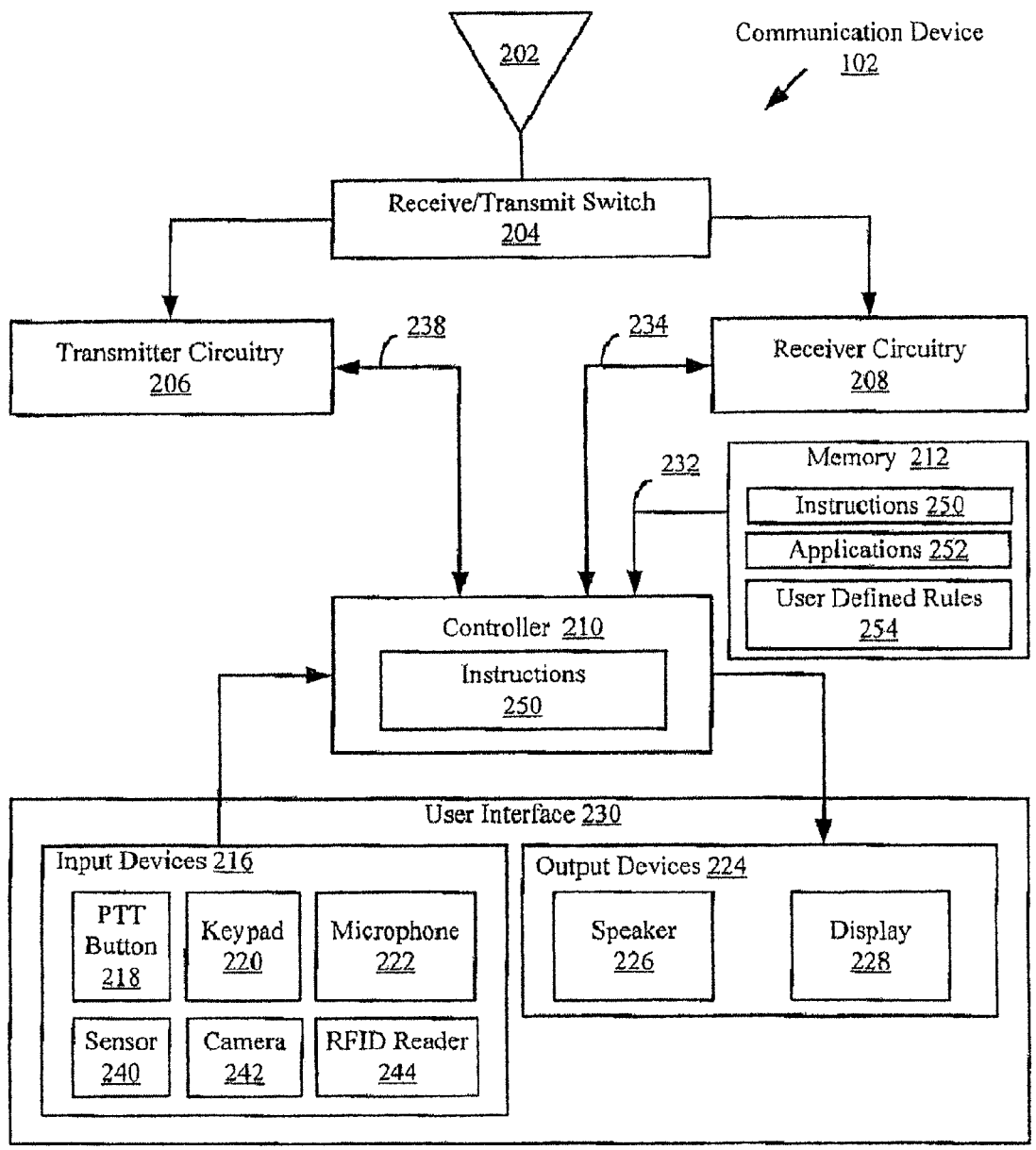
FIG. 2 is a block diagram of an exemplary communication device configured to be implemented into the system of FIG. 1.

Referring now to FIG. 2, there is provided a more detailed block diagram of the communication device 102. The communication device 102 may be, but is not limited to, a mobile phone, a smart phone, a PDA, a tablet Personal Computer ("PC"), or the like. Notably, the communication device 102 can include more or less components than those shown in FIG. 2. For example, the communication device 102 may include a wired system interface, such as a universal serial bus interface (not shown in FIG. 2). The communication device 102 may further include an antenna 202 for receiving and transmitting Radio Frequency (RF) signals, for example. A receive/transmit (Rx/Tx) switch 204 may selectively couple the antenna 202 to a transmitter circuitry 206 and a receiver circuitry 208.

The receiver circuitry 208 may be configured to demodulate and decode the RF signals received from a network (e.g., the network 104 of FIG. 1) to derive information therefrom. The receiver circuitry 208 is coupled to a controller 210 via an electrical connection 234. The receiver circuitry 208 may provide the decoded RF signal information to the controller 210. The controller 210 uses the decoded RF signal information in accordance with the function(s) of the communication device 102. The controller 210 also provides information to the transmitter circuitry 206 for encoding and modulating information into RF signals. Accordingly, the controller 210 is coupled to the transmitter circuitry 206 via an electrical connection 238. The transmitter circuitry 206 may communicate the RF signals to the antenna 202 for transmission to an external device (e.g., network equipment of network 104 of FIG. 1).

The controller 210 may store the decoded RF signal information in a memory 212 of the communication device 102. Accordingly, the memory 212 is connected to and accessible by the controller 210 through an electrical connection 232. The memory 212 can be a volatile memory and/or a non-volatile memory. For example, the memory 212 can include, but is not limited to, a Random Access Memory (RAM), a Dynamic Random Access Memory (DRAM), a Static Random Access Memory (SRAM), Read-Only Memory (ROM), and flash memory. The memory 212 may also have stored therein software applications 252 and user-defined rules 254. The software applications 252 may include, but are not limited to, applications operative to provide telephone services, network communication services, Internet connectivity and access services, commerce services, email services, web based services, and/or electronic calendar services.

As shown in FIG. 2, one or more sets of instructions 250 may also be stored in the memory 212. The instructions 250 can also reside, completely or at least partially, within the controller 210 during execution thereof by the communication device 102 of FIG. 1. In this regard, the memory 212 and the controller 210 can constitute non-transient machine-readable media. The term "machine-readable media", as used here, refers to a single medium or multiple media that store the one or more sets of instructions 250. The term "machine-readable media", as used here, also refers to any medium that is capable of storing, encoding or carrying the set of instructions 250 for execution by the communication device 102 and that cause the communication device 102 to perform one or more of the methodologies of the present disclosure.

The controller 210 is also connected to a user interface 230. The user interface 230 may include input devices 216, output devices 224, and software routines (not shown in FIG. 2) configured for a user to interact with and control the software applications 252 installed on the communication device 102. Such input and output devices respectively include, but are not limited to, a display 228, a speaker 226, a keypad 220, a directional pad (not shown in FIG. 2), a directional knob (not shown in FIG. 2), a microphone 222, a Push-To-Talk ("PTT") button 218, sensors 240, a camera 242, and a Radio Frequency Identification ("RFID") reader 244.

Figure 3:
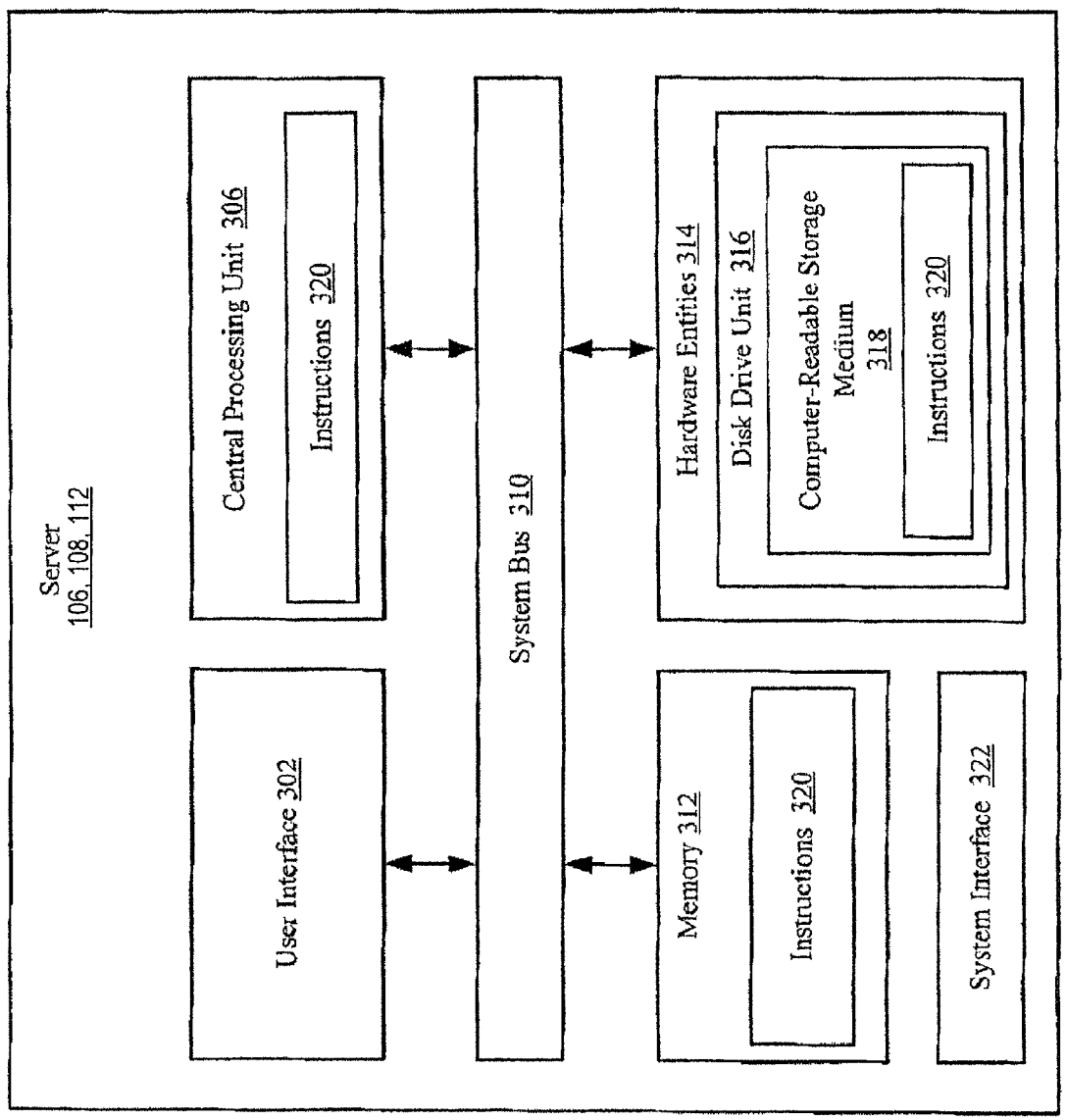
FIG. 3 is a block diagram of an exemplary server configured to be implemented into the system of FIG. 1.

Referring now to FIG. 3, there is provided a more detailed block diagram of the server 106, 108, 112 of FIG. 1. While FIG. 3 illustrates a traditional server architecture, it is noted that other configurations may also be used. For example, some or all of the hardware or software may be distributed among multiple servers. Likewise, functionality may be distributed across or incorporate the use of communications networks including the Internet. To this end, parts or all of the hardware and software described herein may represent so-called "cloud" computing solutions. As another non-limiting example, the user interface may be distributed across multiple devices, including servers, mobile devices, non-mobile computing devices, and the like. Likewise, software may be run as a dedicated application, distributed across remote servers and/or served from the "cloud", run in a browser, or be embodied in a mobile application.

The server 106, 108, 112 may include a system interface 322, a user interface 302, a Central Processing Unit (CPU) 306, a system bus 310, a memory 312 connected to and accessible by other portions of the server 106, 108, 112 through the system bus 310, and hardware entities 314 connected to the system bus 310. At least some of the hardware entities 314 perform actions involving access to and use of the memory 312, which can be a Random Access Memory (RAM), a disk driver and/or a Compact Disc Read Only Memory (CD-ROM). Some or all of the listed components 302-322 can be implemented as hardware, software and/or a combination of hardware and software. The hardware includes, but is not limited to, an electronic circuit.

The server 106, 108, 112 may include more, less or different components than those illustrated in FIG. 3. The hardware architecture of FIG. 3 represents one embodiment of a representative server configured to provide supporting services to a user of a communication device (e.g., communication device 102 of FIG. 1). For example, the server 106, 108, 112 may implement a method for lookup of available auctions using an external database in communication with the server 106, 108, 112 (database not depicted), or the server may use its existing disk drive unit 316, computer-readable storage medium 318 and other facilities to store auction information, as needed. It may also provide dosage factor data to the communication device 102, as needed. Exemplary embodiments of said method will be described below in relation to FIGS. 4-5.

Hardware entities 314 can include microprocessors, Application Specific Integrated Circuits (ASICs) and other hardware. Hardware entities 314 can include a microprocessor programmed for facilitating the provision of the automatic software function control services to a user of the communication device (e.g., communication device 102 of FIG. 1). In this regard, it should be understood that the microprocessor can access and run various software applications (not shown in FIG. 3) installed on the server 106, 108, 112. Such software applications include, but are not limited to, database applications.

As shown in FIG. 3, the hardware entities 314 can include a disk drive unit 316 comprising a computer-readable storage medium 318 on which is stored one or more sets of instructions 320 (e.g., software code or code sections) configured to implement one or more of the methodologies, procedures, or functions described herein. The instructions 320 can also reside, completely or at least partially, within the memory 312 and/or within the CPU 306 during execution thereof by the server 108. The memory 312 and the CPU 306 also can constitute machine-readable media. The term "machine-readable media", as used here, refers to a single medium or multiple media (e.g., a centralized or distributed database, and/or associated caches and servers) that store the one or more sets of instructions 320. The term "machine-readable media", as used here, also refers to any medium that is capable of storing, encoding or carrying a set of instructions 320 for execution by the server 106, 108, 112 and that cause the server 106, 108, 112 to perform any one or more of the methodologies of the present disclosure.

Figure 4:
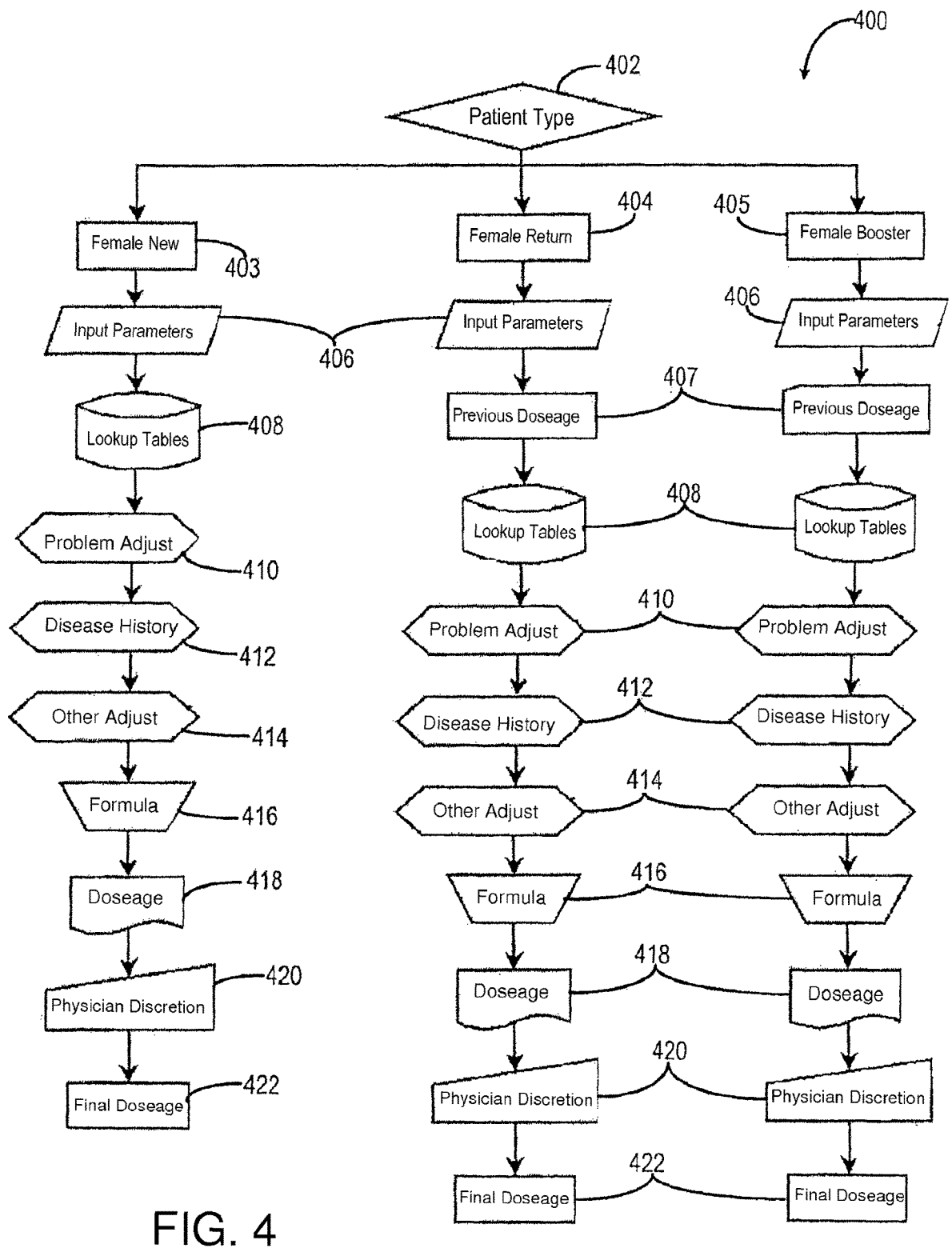
FIG. 4 is a flow chart setting forth the steps of processes for determining a dosage for hormone replacement therapy for a female patient in accordance with the present invention.
Figure 5:
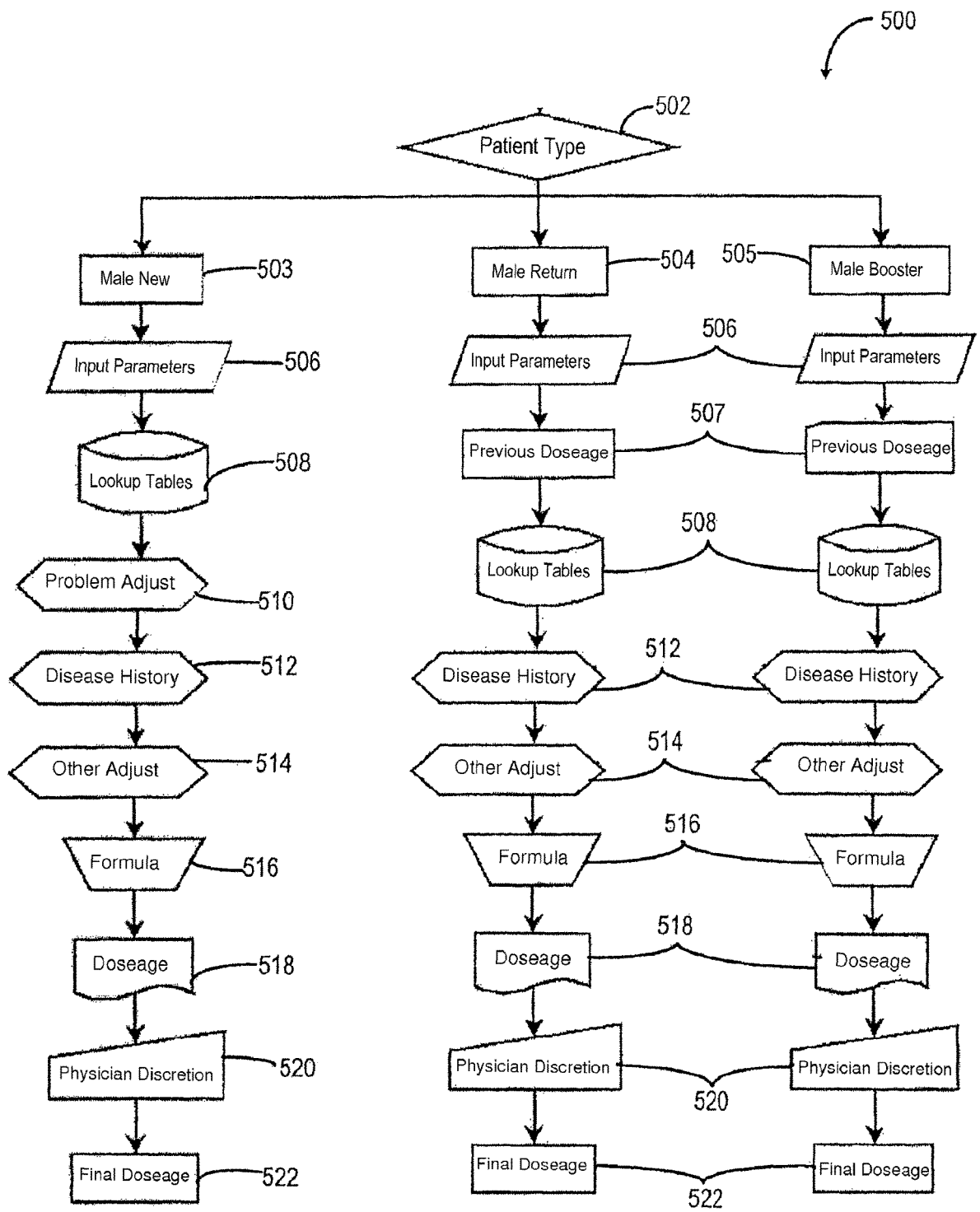
FIG. 5 is a flow chart setting forth the steps of processes for determining a dosage for hormone replacement therapy for a male patient in accordance with the present invention.

Referring now to FIGS. 4-5, flow charts setting forth exemplary steps 400, 500 for determining a dosage for hormone replacement therapy are provided. Exemplary embodiments of the disclosure are presented in FIGS. 4-5 with respect to methods for calculating hormone replacement therapy (HRT) dosage, in particular for calculation of SOTTOPELLE (TM) HRT dosage. References to "HRT" in the descriptions to FIGS. 4-5 herein are understood to specifically refer to SOTTOPELLE (TM) HRT, unless otherwise indicated. It is understood that the tables, lookup values, factors used in these embodiments may vary depending on several variables, such as but not limited to therapy regimens, drug used, drug concentration, absorption, efficacy, and the like.

Although use of a communication device 102, as described in FIG. 2, is presented herein, the present disclosure is not limited in this regard. The methods are useful with alternative devices as well, such as portable computer applications, PDA applications, and tablet computing devices, and the like. The exemplary steps 400, 500 described in FIGS. 4-5 may be performed by an electronic circuit of the communication device 102, with the assistance of the physician 110, servers 106, 108, 112, database 114 and network 104, consistent with an embodiment of the disclosure.

Returning to FIG. 4, to start the process for determining the dosage for a female patient, a patient type is identified at decision block 402. The patient type may be determined by the electronic circuit, as previously described with respect to FIG. 3. Additionally, or alternatively, the physician 110 of FIG. 1 may manually input the patient type directly into the communication device 102 or, the patient type may be determined from the patient name and/or a unique identification number combined with a lookup of patient information stored in the database 114. The patient types identified at block 402 may include: A Female New Patient, as shown at process block 403, which may be a female patient that has never been treated with HRT or someone who has not received pellets for over ten months; A Female Return Patient, as shown at process block 404, which may be a female patient that has been treated with HRT and is returning for ongoing treatment; Or a Female Booster Patient, as shown at process block 405, which may be a female patient that has been treated with HRT needing an additional dose prior to the patient's next dose.

Once the patient type is identified, input parameters may be input into the communication device, regardless of which patient type is identified, at process block 406. The input parameters may include, but are not limited to, patient age, height, weight, race, number of pregnancies, number of live births, number of abortions, history of renal disease, active liver disease, history of hysterectomy, history of cervical cancer, history of ovarian cancer, history of fibrocystic breast disease, history of breast cancer, current follicle stimulating hormone (FSH) level, current testosterone level, current estradiol level, current non-pellet estradiol dose, history of acne or facial hair, history of hair loss, history of polycystic ovary syndrome (PCOS), history of heavy menses/fibroids, and history of metabolic syndrome.

If the patient type is a Female New Patient at block 403, once the input parameters are input at process block 406, various lookup tables may be consulted by the electronic circuit to determine various factors for estradiol and testosterone dosage calculation as well as dosage adjustment factors for various conditions and problems at process block 408. Exemplary lookup tables used in an embodiment of the disclosure for female patients are shown below and may include Female Estradiol Weight/Age (Table 1), Female Estradiol Age (Table 2), Female Estradiol FSH (Table 3), Female Testosterone Weight (Table 4), Female Testosterone Age (Table 5), Female Testosterone Testosterone (Table 6), Conjugated Estrogen, Estradiols Pills, Estradiol Patch, Biestradiol Cream or Tabs, and Problem Factor. Exemplary tables used for HRT follow:

TABLE 1

Female Estradiol Weight/Age

| Weight/Age Ratio (lbs/Years) | Lookup Value (mg) |
|---|---|
| 0-1.5 | 1 |
| 1.6-2.5 | 2 |
| 2.6-3.9 | 3 |
| >4 | 2 |

TABLE 2

Female Estradiol Age

| Age (Years) | Lookup Value |
|---|---|
| <40 | 3 |
| 40-50 | 5 |
| 51-60 | 15 |
| 61-68 | 12.5 |
| >68 | 4 |

TABLE 3

Female Estradiol FSH

| FSH | Lookup Value |
|---|---|
| <31 | 0 |
| 31-50 | 1 |
| 51-100 | 2 |
| >100 | 3 |

TABLE 4

Female Testosterone Weight

| Weight (lbs.) | Lookup Value (mg) |
|---|---|
| 75-150 | 75 |
| 151-200 | 87.5 |
| >200 | 100 |

TABLE 5

Female Testosterone Age

| Age (Years) | Lookup Value |
|---|---|
| 0-67 | 1 |
| >67 | 0.63 |

TABLE 6

Female testosterone Testosterone

| Testosterone | Lookup Value (mg) |
|---|---|
| 0-20 | 37.5 |
| 21-100 | 25 |
| >100 | 0 |

After obtaining the lookup values from the various tables at process block 408, additional problem adjustment factors may be determined at process block 410, disease history may be factored in at process block 412, and other adjustments may be determined at process block 414. In an embodiment of the disclosure, these various considerations may include, but are not limited to: Female Estradiol Problem Factor, Conjugated Estrogen, Estradiols Pills, Estradiol Patch, Biestradiol Cream or Tabs, and Problem Factor. Exemplary adjustment factors applied to the dosage determined after application of the lookup values to the base dosage, i.e., "test dosage" may include, but are not limited to: for history of acne or facial hair, dosage=test dosage× 0.90; history of hair loss, dosage=test dosage×0.88; hysterectomy, if YES, dosage=test dosage×0.88; history of PCOS, dosage=test dosage×0.75; history of heavy menses, if YES, dosage=test dosage×0.88; history of metabolic syndrome, if YES, DO NOTHING; persistent breast pain, if YES, dosage=test dosage×0.80; mid-cycle bleeding, if YES, dosage=test dosage×0.80; headache, if YES, dosage=test dosage×0.75; fluid retention, if YES, dosage=test dosage× 0.75; and, fibrocystic breast disease, if YES, dosage=test dosage×0.70. Also, if the FSH is >=30 and age is between 20 and 50 years, then the FSH adjustment lookup value is set to 12.5. In another non-limiting example, the FSH adjustment lookup is set to a value 10 and 35 is the age is greater that or equal to 30.

Next, at process block 416, formula may be applied to determine female dosage for estradiol and testosterone.

Female dosage calculations involve two calculations, one for estradiol and the other for testosterone. The estradiol calculation involves calculating the weight/age ratio, age, current FSH levels, a problem factor multiplier and an FSH adjustment factor. The weight/age ratio is calculated by dividing the weight in pounds by the age in years. As indicated above, the weight/age ratio is then used to lookup the weight/age ratio lookup value from Table 1. The age is then used to lookup the lookup value in the Female Estradiol Age lookup table (Table 2). The value of the current FSH level is then used to find the corresponding lookup value in the Female Estradiol FSH lookup table (Table 3). These values are then summed into a single value and then multiplied by any problem factor adjustment values from process block 410, and added to the calculation. The estradiol dosage is thus calculated in Equation (1) as:

$$\text{Estradiol dosage} = ((\text{Weight Age Ratio Lookup} + \text{Age Lookup} + \text{FSH Lookup}) \times \text{Problem Factor}) + \text{FSH Adjustment}$$

In one non-limiting example, the FSH lookup and the FSH adjustment for calculating the estradiol dosage for female new or female return patients accounts for more that 50% of the estradiol dosage.

Similarly, the testosterone calculation involves calculating the weight lookup value, current testosterone level lookup value and testosterone age lookup value. The weight is used to obtain a value from the Female Testosterone Weight lookup table (Table 4). The current testosterone level is used to obtain a value in the Female Testosterone Testosterone lookup table (Table 5). These two values are then summed. The age is used to obtain a value in the Female Testosterone Age lookup table (Table 6). The obtained testosterone age lookup value is then multiplied by the sum of the testosterone weight and testosterone lookup values. The testosterone dosage is thus calculated in Equation (2) as:

$$\text{Testosterone dosage} = (\text{Weight Testosterone Lookup} + \text{Testosterone Level Lookup}) \times \text{Testosterone Age Lookup}$$

Once the dosage is calculated at process block 418, exception logic may be applied at process block 420 at the physician's discretion, for example, for pre-menopausal women. For example, pre-menopausal females do not receive estradiol except in the case where current estradiol level is <10 or if the pre-menopausal female patient exhibits symptoms of migraines. For pre-menopausal women without estradiol level <10 or migraines, estradiol calculated dose becomes 0.00. At process block 422, a final dosage for the new female patient is determination.

Like the dosage calculations for female new patients, female return dosage calculations, as indicated at process block 404, also involve two components: one for estradiol and the other for testosterone. The method includes all the steps included for a new patient, and also determining the patient's previous dosage at process block 407 after receiving the input parameters at process block 406. The previous dosage obtained at process block 407 may be directly input or may be saved in the database 114 of FIG. 1. The female return patient estradiol dosage is then calculated at process block 416 using the following Equation (3):

$$\text{Estradiol dosage} = ((\text{Weight Age Lookup} + \text{Age Lookup} + \text{FSH Lookup} + \text{Current Dose Lookup}) \times \text{Problem Factor})$$

Female Return Testosterone dosage is calculated using the following Equation (4):

$$\text{Testosterone dosage} = (\text{Weight Testosterone Lookup} + \text{Testosterone Level Lookup}) \times \text{Testosterone Age Lookup}$$

Calculation of female booster dosages, as shown at process block 405, for estradiol and testosterone is determined at process block 416, respectively, by taking the previous estradiol dosage and dividing by 2.00, and taking the previous testosterone dosage and dividing by 3.00. In another non-limiting example, the estradiol and testosterone is determined at process block 416, respectively, by taking the previous estradiol dosage and dividing by a value that is greater than or equal to 1.5 and less than or equal to 3.0, and taking the previous testosterone dosage and dividing by a value that is greater than or equal to 1.5 and less than or equal to 5.0.

Referring now to FIG. 5, the exemplary steps 500 for determining the dosage for a male patient are provided. To start the process for determining the dosage for the male patient, a patient type is identified at decision block 502. The patient type may be determined by the electronic circuit, as previously described with respect to FIG. 3. Additionally, or alternatively, the physician 110 of FIG. 1 may manually input the patient type directly into the communication device 102 or, the patient type may be determined from the patient name and/or a unique identification number combined with a lookup of patient information stored in the database 114. The patient types identified at block 502 may include: A Male New Patient, as shown at process block 503, which may be a male patient that has never been treated with HRT or someone who has not received pellets for over ten months; A Male Return Patient, as shown at process block 504, which may be a male patient that has been treated with HRT and is returning for ongoing treatment; Or a Male Booster Patient, as shown at process block 505, which may be a male patient that has been treated with HRT needing an additional dose prior to their next dose.

Once the patient type is identified, input parameters may be input into the communication device, regardless of which patient type is identified, at process block 506. The input parameters may include, but are not limited to, patient age, height, weight, race, history of hypertension, history of diabetes, history of colon cancer, history of testicular cancer, history of BPH, history of metabolic syndrome, physical activity level, history of prostate cancer, history of renal disease, active liver disease and current testosterone level.

If the patient type is a Male New Patient at block 503, once the input parameters are input at process block 506, various lookup tables may be consulted by the electronic circuit to determine a base dosage for testosterone and adjustment factors for various conditions and problems. Exemplary lookup tables used in an embodiment of the disclosure for male patients include Male Age and Male Weight, Exemplary tables used for HRT follow:

TABLE 7

Male Age

| Age (Years) | Lookup Value |
|---|---|
| <69 | 1 |
| >68 | 0.8 |

TABLE 8

Male Weight

| Weight (lbs.) | Lookup Value (mg) |
|---|---|
| <151 | 1200 |
| 151-175 | 1400 |
| 176-200 | 1600 |
| 201-225 | 1800 |
| 226-250 | 2000 |
| 251-275 | 2200 |
| 276-300 | 2400 |
| 301-350 | 2600 |
| 351-400 | 2800 |
| >400 | 3000 |

After obtaining the lookup values from the various tables at process block 508, additional problem adjustment factors are determined at process block 510, disease history is factored in at process block 512, and other adjustments are determined at process block 514. In an embodiment of the disclosure, these various considerations may include, but are not limited to: Diabetes and Metabolic Syndrome. In the case of Diabetes or Metabolic Syndrome, the testosterone dosage is increased by 100 milligrams (mg), for example. Exemplary adjustment factors applied to the dosage determined after application of the lookup values to the base dosage, i.e., "test dosage" may include, but are not limited to: for history of BPH, dosage=test dosage×0.95; history of prostate cancer, dosage=test dosage×0.90; history of both prostate cancer and BPH, dosage=test dosage×0.90; physical activity level: sedentary/work only, decrease dosage by 100 mg, work+exercise 5 times/week, increase dosage by 100 mg; testosterone level >=700, no treatment; monthly testosterone injection (100-200 mg), no change in dosage; weekly testosterone injection (100-200 mg), increase dosage by 100 mg; testosterone gel (1.62%) used, increase dosage by 100 mg.

Next, at process block 516, formula may be applied to determine male dosage for testosterone HRT. Male dosage calculations involve a single calculation for testosterone. The testosterone calculation involves calculating the weight lookup value, age lookup value, obtaining the current testosterone dose value, if any, and applying any additional adjustments (from above). As indicated above, the age is used to lookup the age lookup value from Table 7. In one example, if the age lookup value is greater than or equal to 65, the testosterone dosage for a male new, return or booster patient is between 10% and 50% less. The weight is then used to lookup the lookup value in the Male Weight lookup table (Table 8). These values are then multiplied together with the applicable adjustment factor to determine the testosterone dosage. The testosterone dosage is thus calculated in Equation (5) as:

Testosterone dosage=Age Testosterone Lookup× Weight Testosterone Lookup×other Adjustment Multiplication Factor Dosage calculations for male return patients, as shown at process block 504, are provided at process block 507 by application of the following Equation (6):

If Current Testosterone Dosage < 400.00 mg, then
    Return Testosterone dosage = previous Testosterone Dosage + a value ≥ 200 and ≤ 1000 mg;
Else
    Return Testosterone dosage - previous Testosterone Dosage Male booster testosterone dosage, as shown at process block 505, is dependent on existing or previous historical conditions such as BPH, cancer or combinations thereof, as included in the adjustment factor calculated for male new patients, above. The booster testosterone dosage is then determined in Equation (7) as:

Booster testosterone dosage=previous testosterone dosage×(0.20×adjustment Multiplication Factor)

In other embodiments, the male booster testosterone dosage may be determined in equation (8) as:

Booster testosterone dosage=previous testosterone dosage×(a value ≥0.20 and ≤90 mg)×(adjustment Multiplication Factor)

Figure 6:
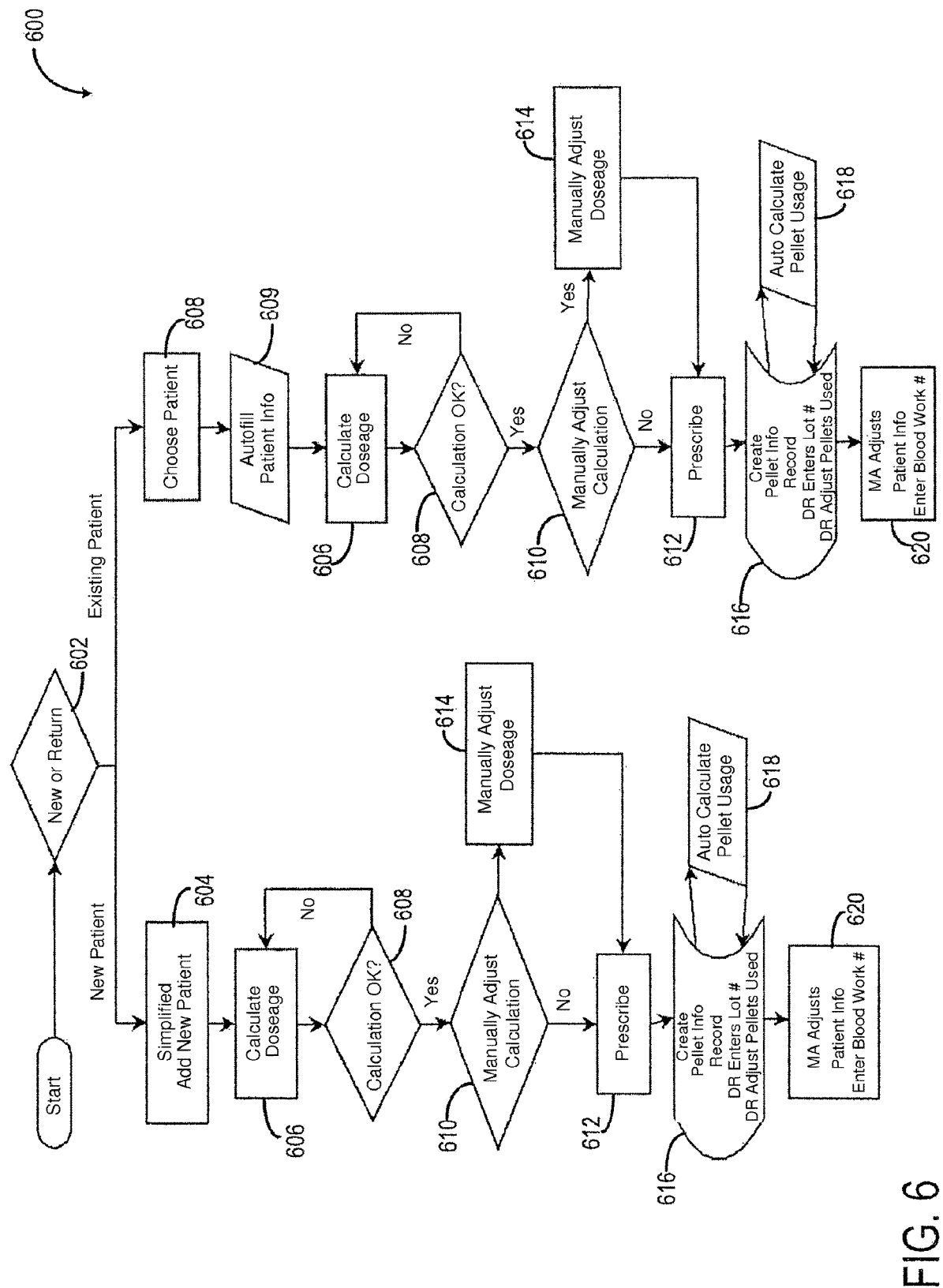
FIG. 6 is a flow chart setting forth the steps of processes for automatically calculating an accurate recommended dosage for hormone replacement therapy and automating a life cycle of a patient's treatment over time in accordance with another aspect of the present invention.
Figure 7:
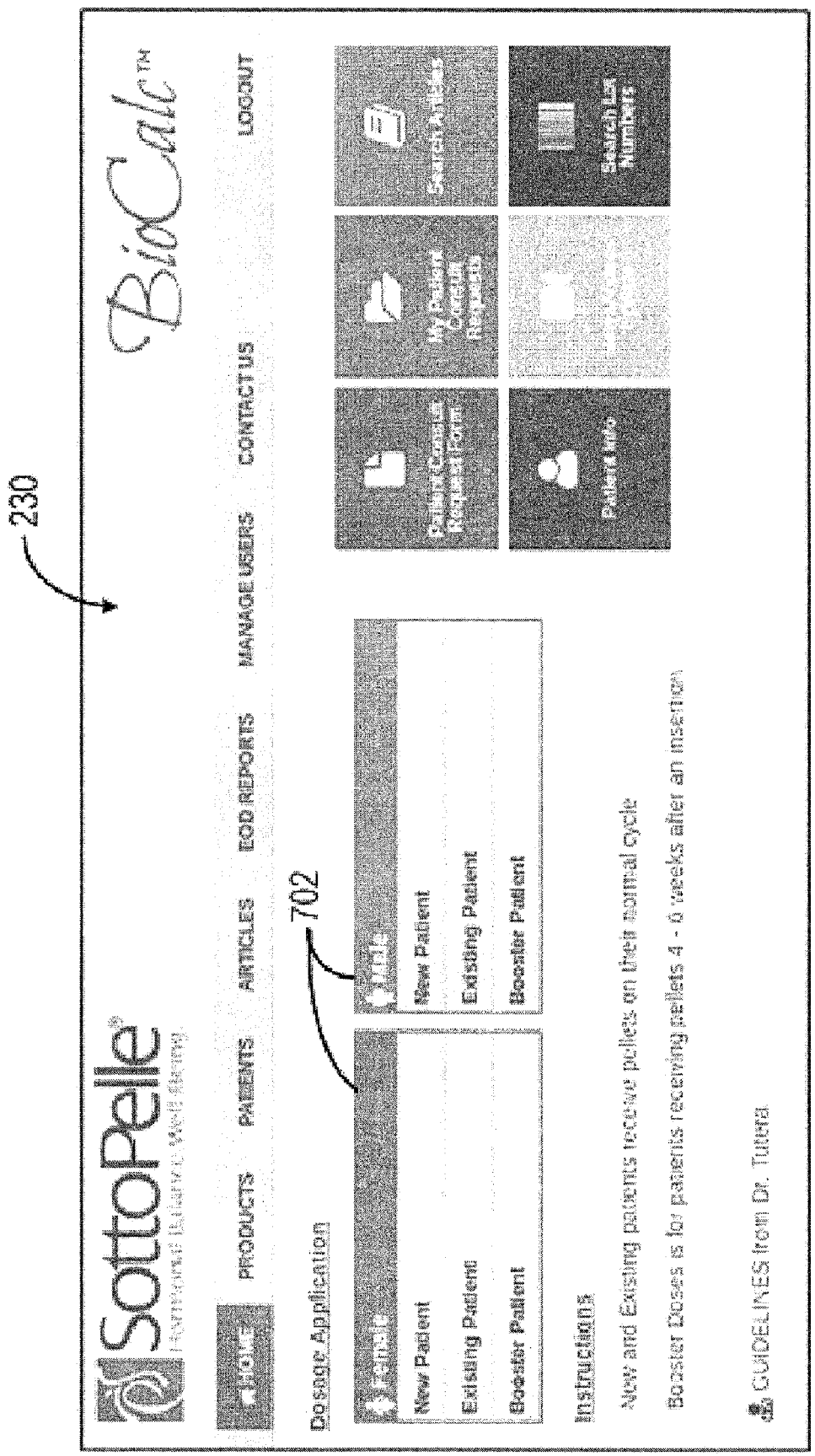
FIG. 7 is an exemplary screen shot of a user interface of the communication device that prompts a user to select a patient type.

Turning now to FIG. 6, a flow chart setting forth exemplary steps 600 for automatically calculating an accurate recommended dosage for HRT and automating a life cycle of a patient's treatment over time is provided. To start the process, a patient type is obtained at decision block 602. The patient type may be determined by the user, such as the physician 110 of FIG. 1, for example, who may be prompted by the system to input the patient type directly into the user interface of the communication device 102 of FIG. 1, for example. As shown in FIG. 7, an exemplary user interface 230 of the communication device 102 is provided that prompts the user to select one of the patient types 702. The patient types 702 may include a Female New Patient, a Female Existing/Return Patient, a Female Booster Patient, a Male New Patient, a Male Existing/Return Patient, and a Male Booster Patient.

Figure 8:
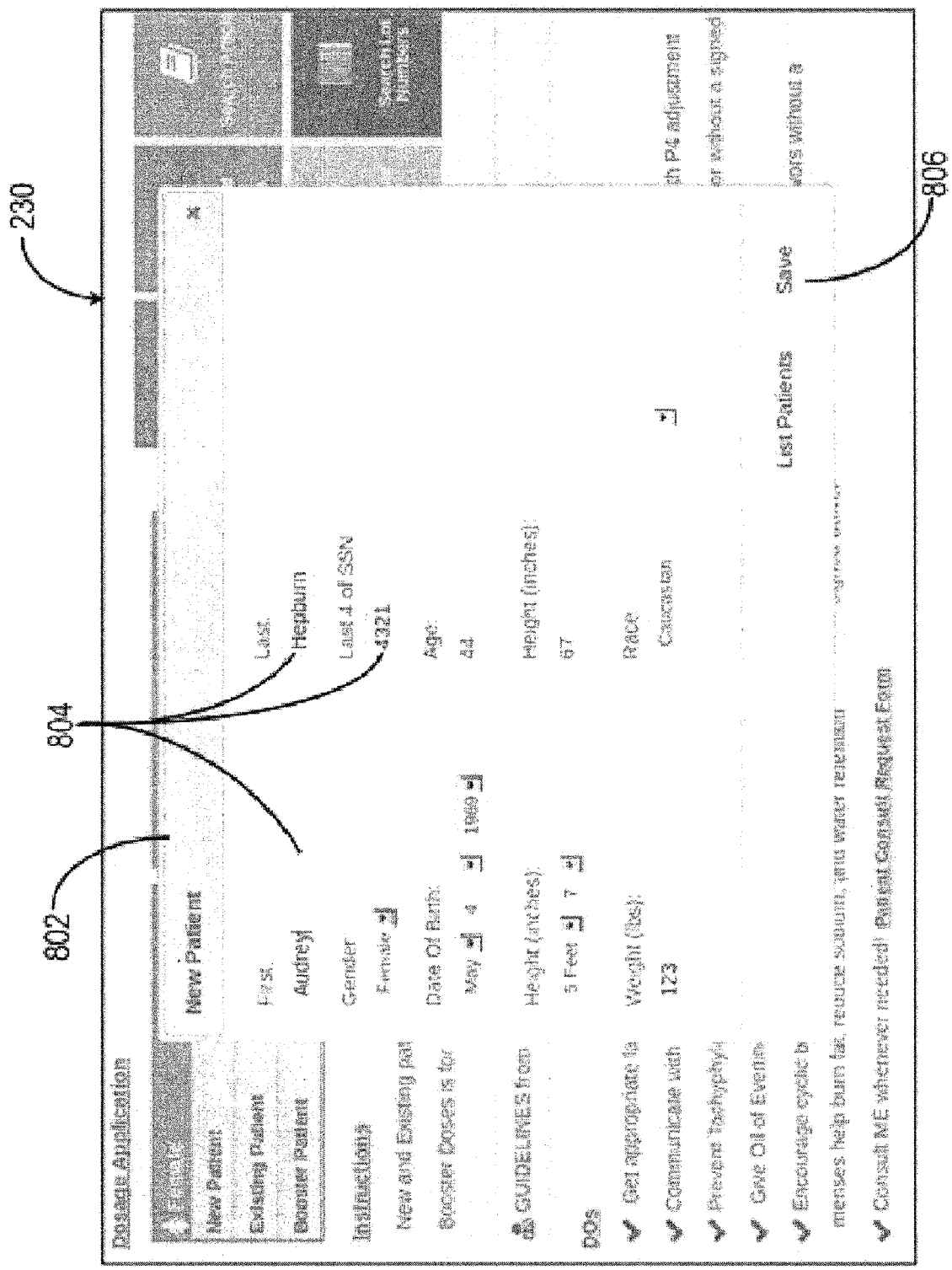
FIG. 8 is an exemplary screen shot of a new patient dialog screen displayed on the user interface.

Returning to FIG. 6, once the patient type is selected by the user, the system controller 210 may access the set of instructions 250, as shown in FIG. 2, to automatically determine whether the patient is a new or existing patient at decision block 602. If the patient is a new patient at decision block 602, the system may prompt the user to add the new patient's information at process block 604. In one embodiment, the user may enter the new patient information prior to the patient's appointment so that the user may select the newly entered patient to calculate dosing, as shown at process block 606, ahead of time. When the user selects a new patient on the user interface 230 shown in FIG. 7, a new patient dialog screen 802 may be activated on the user interface 230, as shown in FIG. 8. Several fields 804 may be provided on the new patient dialog screen 802 for the user to fill in. The fields 804 may include, but at not limited to first name, last name, last four digits of the patient's social security number, date of birth, height, and race of the patient. Once the user enters the patient's date of birth and height into the corresponding fields 804, the age in years and the height in inches, for example, may be automatically calculated by the set of instructions stored in the system. Once the necessary new patient information is obtained, the user may click a save button 806 that will save the patient information in the database 114, of FIG. 1, and open a new patient dosage calculation page, as will described in further detail below.

Figure 9:
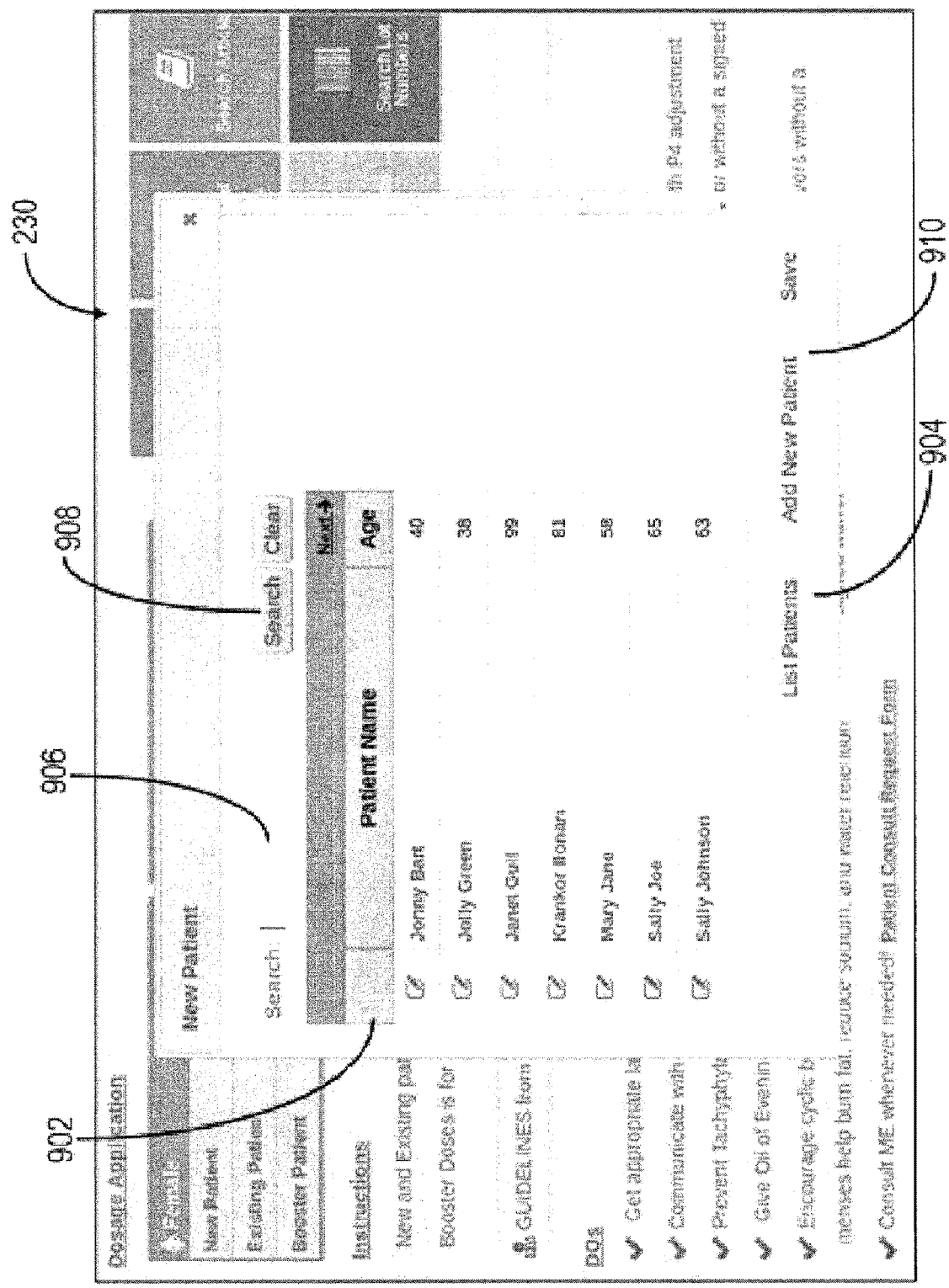
FIG. 9 is an exemplary screen shot of a patient list displayed on the user interface.

When the new patient's information is entered into the system by the user ahead of time (i.e., prior to the patient's appointment), the user may be provided with an exemplary patient list 902 displayed on the user interface 230, as shown in FIG. 9. The patient list 902 may be presented to the user after selecting a list patients button 904, which generates a list of patients stored in the system database. The user may then choose the previously entered patient by using a search input field 906 and clicking a search button 908 to find the newly entered patient. The new patient may be selected, for example, by clicking on the patient name displayed in the patient list 902, and the new patient dosage calculation may be initiated at process block 606, as will be described in further detail below. In addition, an add new patient button 910 may be provided on the user interface 230 of FIG. 9 to allow the user to create a new patient record. This may be the case, for example, if the user thought he/she entered the new patient's information prior to the patient's appointment, but in reality did not. Clicking the add new patient button 910 will direct the user back to the new patient dialog screen 802 shown in FIG. 8.

Figure 10:
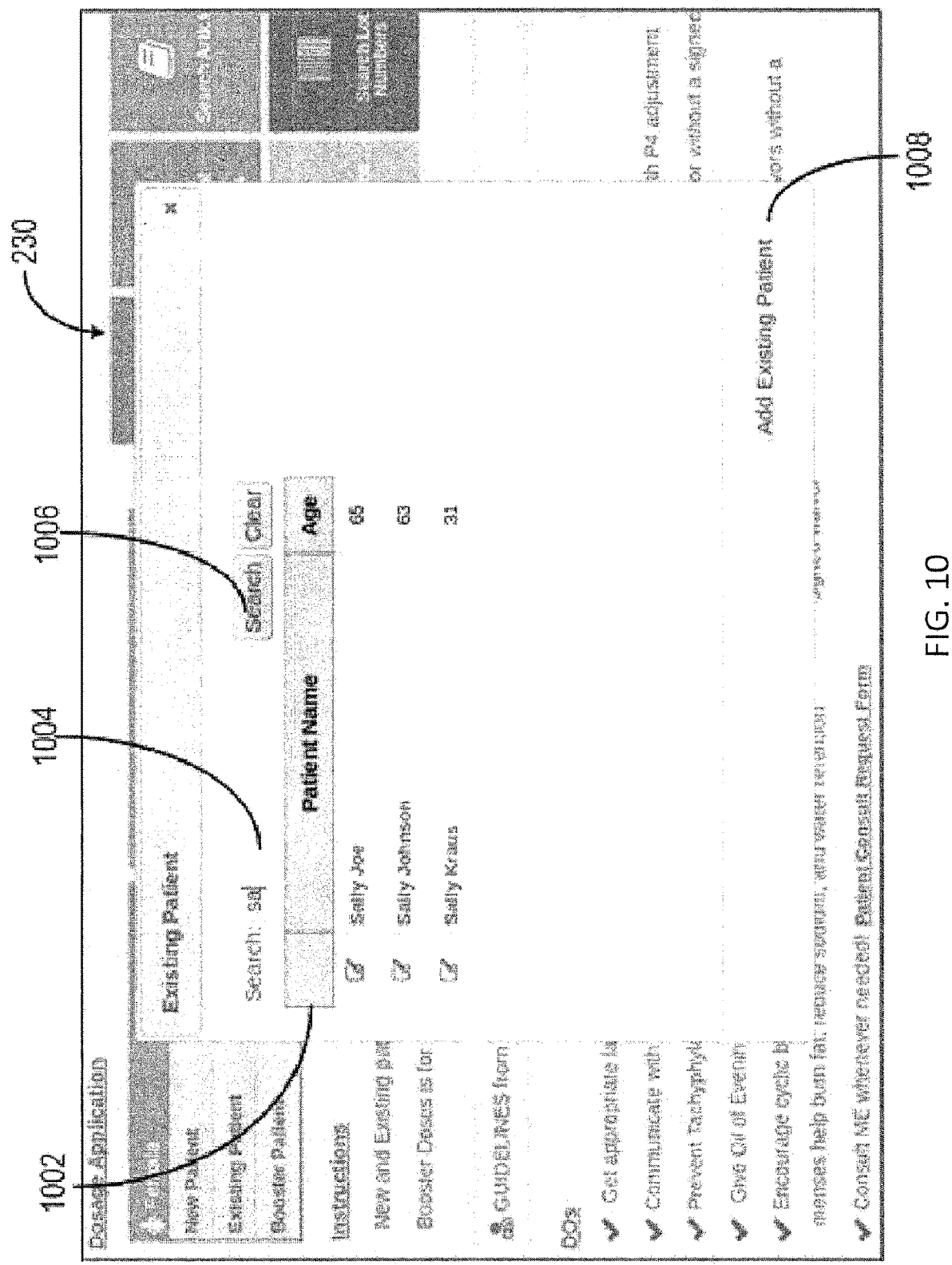
FIG. 10 is an exemplary screen shot of a patient list displayed on the user interface that may be presented to the user after searching for an existing patient.

Returning to FIG. 6, if the patient is an existing patient at block 602, the system may prompt the user to select the existing patient from a patient list, for example, at process block 608. FIG. 10 shows an exemplary patient list 1002 displayed on the user interface 230 that may be presented to the user after searching for an existing patient using a search input field 1004 and clicking a search button 1006. The user may then choose an existing patient from the patient list 1002 at process block 608. Additionally, the set of instructions stored on the system controller can determine, based on dosing history and demographics, for example, if the calculation is a Female New Patient, a Female Existing/Return Patient, a Female Booster Patient, a Male New Patient, a Male Existing/Return Patient, and a Male Booster Patient.

Figure 11:
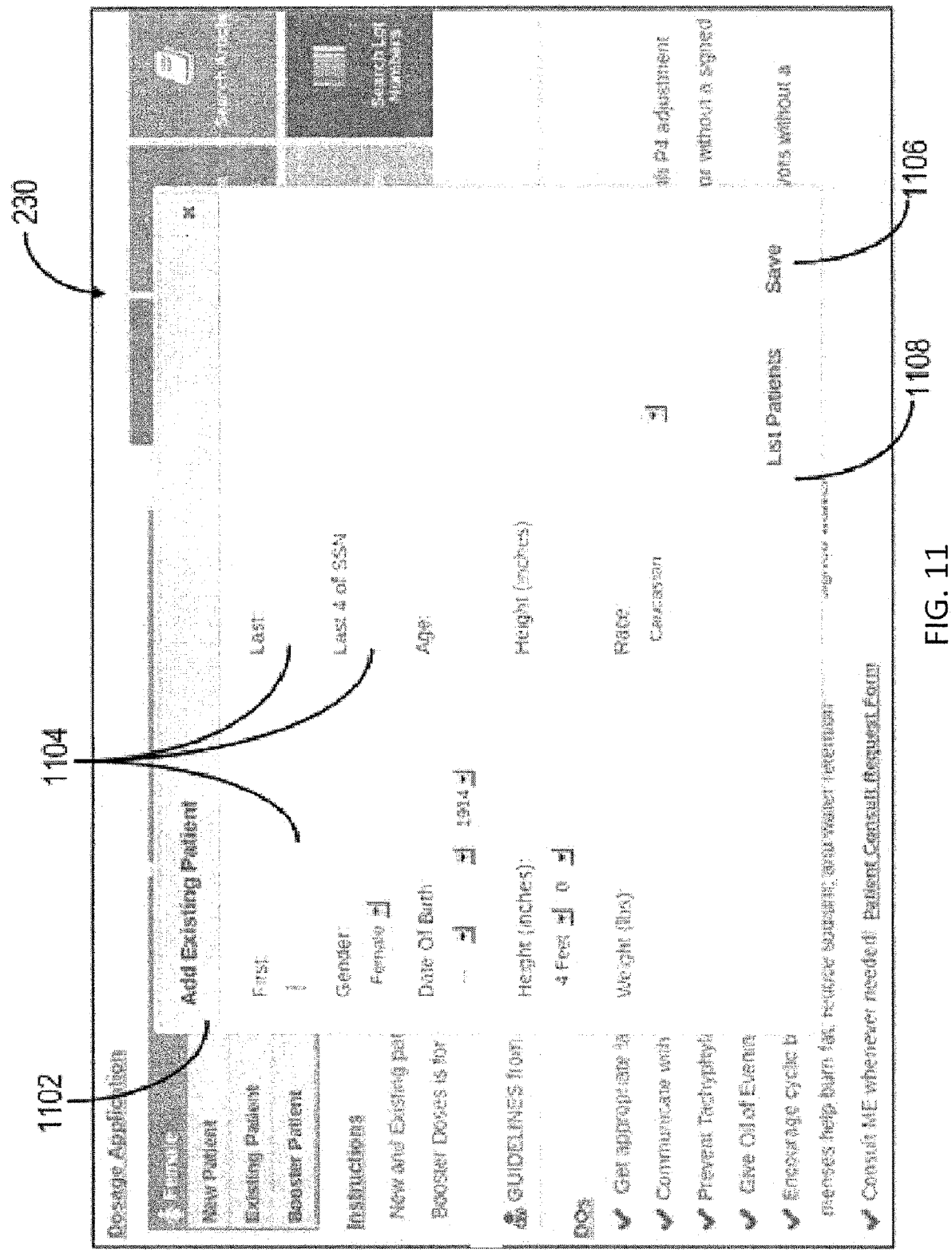
FIG. 11 is an exemplary screen shot of an existing patient dialog screen displayed on the user interface.

In the case where a returning patient has not previously been entered into the system, the user may select an add existing patient button 1008 on the bottom to activate an existing patient dialog screen 1102 on the user interface 230, as shown in FIG. 11. Several fields 1104 may be provided on the existing patient dialog screen 1102 for the user to fill in. The fields 1104 may include, but at not limited to first name, last name, last four digits of the patient's social security number, date of birth, height, and race of the patient. Once the user enters the patient's date of birth and height into the corresponding fields 1104, the age in years and the height in inches, for example, may be automatically calculated by the set of instructions stored in the system. Once the necessary patient information is obtained, the user may click a save button 1106 that will save the patient information in the database 114, of FIG. 1, and open a patient dosage calculation page, as will described in further detail below. If, however, the user decides to select an existing patient from the list, a list patients button 1108 may be provided on the existing patient dialog screen 1102 to return to the patient list 1002 shown in FIG. 10.

Returning to FIG. 6, once the existing patient is chosen at process block 608, the set of instructions 250, as shown in FIG. 2, are configured to automatically fill in patient information at process block 609 based on patient records, patient medical history, previous dosing calculations, and historical hormone insertions, for example. Thus, dosage accuracy may be increased by minimizing errors on the dosing input screen and the amount of effort required to calculate a dose may be decreased. Patient information obtained from the patient's records that may automatically filled in at process block 609 may include, but is not limited to, patient age, weight, height, and race. Patient information obtained from the patient's medical history or the patient's previous dosing calculations that may be automatically filled in at process block 609 may include, but is not limited to, number of pregnancies, number of live births, number of abortions/miscarriages, history of renal disease, active liver disease, hysterectomy, history of cervical cancer, history of ovarian cancer, fibrocystic breast disease, history of breast cancer, can, facial hair, hair loss, history of PCOS, history of heavy menses/fibroids, history of metabolic syndrome, premenopausal, and menstrual migraines.

Thus, in one non-limiting example, if the patient has a history of renal disease, the electronic circuit may be configured to store this medical history corresponding to the patient. The electronic circuit may further be configured to automatically display this relevant medical history corresponding to the patient on the user interface for subsequent dosing since, once identified, the patient will always have a history of renal disease.

Figure 12:
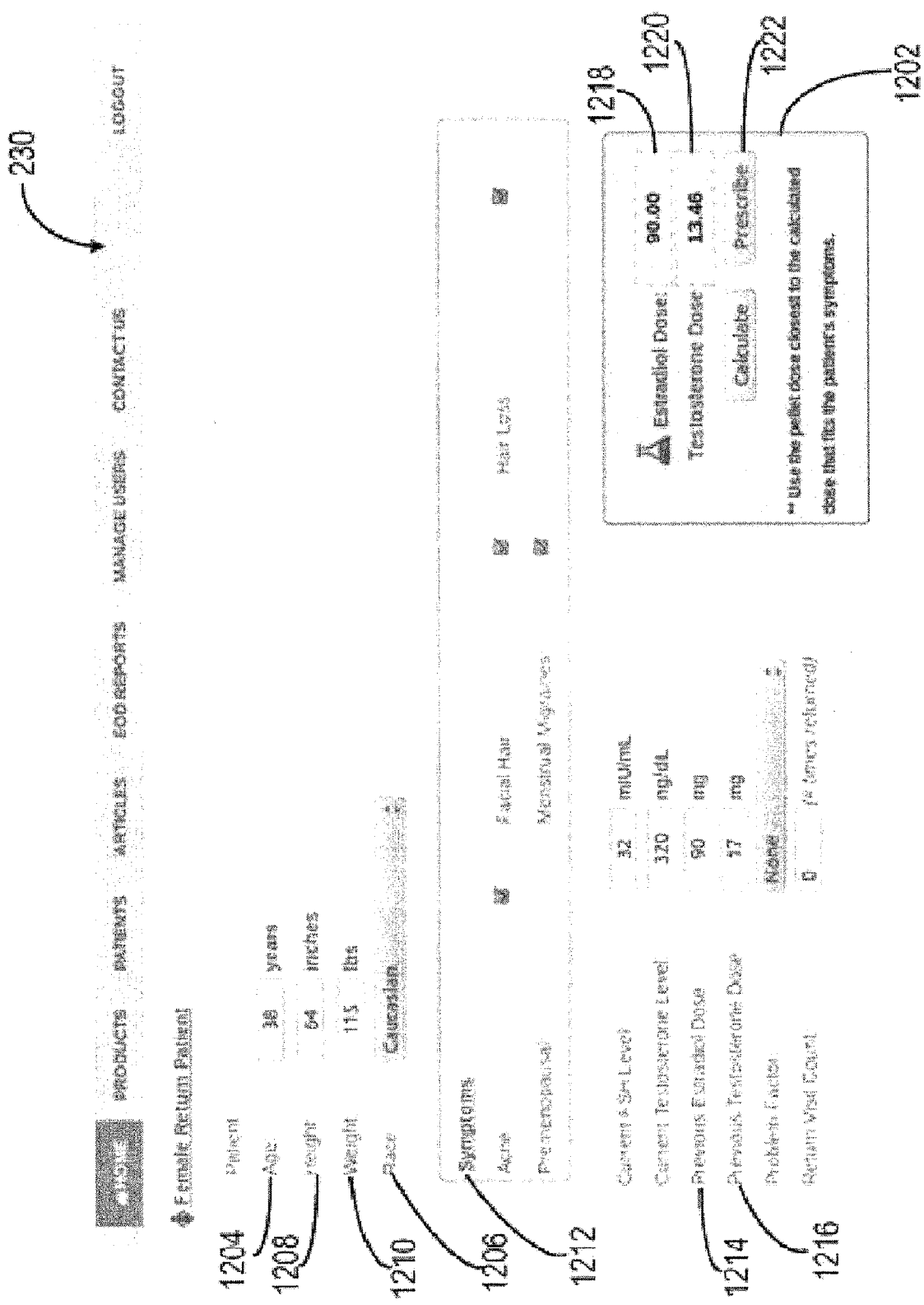
FIG. 12 is an exemplary screen shot of a dosing calculation page that may be displayed to the user on the user interface once patient information has been entered or selected.

FIG. 12 shows an exemplary dosing calculation page 1202 that may be displayed to the user on the user interface 230 once the patient information has been entered or selected. In addition, many of the values on the dosing calculation page 1202 may automatically be filled in. For example, age 1204 may automatically be calculated from the date of birth previously acquired, and race 1206, height 1208, and weight 1210 may automatically be filled in per the patient's stored profile. In one embodiment, weight 1210 may be changed directly on the dosing calculation page 1202, as weight may fluctuate with each visit. Symptoms 1212 may also automatically be filled in per the latest dosage calculation on record. Previous Estradiol dose 1214 may automatically be filled in based on the last full dosage on file for the return or booster patient. The system uses the actual historical inserted dose based on the pellets inserted to calculate the previous estradiol dose 1214. The previous estradiol dose 1214 is different from the calculated estradiol dose 1218 since it is often not possible to obtain the exact calculated dose as the pellets are in discrete amounts, as will be discussed in further detail below. Thus, the last full-dose (i.e., the non-booster dose) is used to calculate the previous estradiol dose 1214. Alternatively, the previous estradiol dose 1214 can be manually changed for the purposes of the dose calculation. Previous Testosterone dose 1216 may also automatically be filled in based on the last full dosage on file for the return or booster patient. The system uses the actual historical inserted dose based on the pellets inserted to calculate the previous testosterone dose 1216. The previous testosterone dose 1216 is different from the calculated testosterone dose 1220 since it is often not possible to obtain the exact calculated dose as the pellets are in discrete amounts. Thus, the last full-dose (i.e., the non-booster does) is used to calculate the previous testosterone dose 1216. Alternatively, the previous testosterone dose 1216 can be manually changed for the purposes of the dose calculation.

Returning again to FIG. 6, once the patient information is added at process block 604 for a new patient, or automatically filled in at process block 609 for an existing patient, the dosage may be calculated at process block 606. The dosage calculation may be computed for both new and existing patients at process block 606, and thus, the same reference numerals will be used to describe the remaining steps 600 of the process. In one embodiment, the dosage may be calculated as previously described with respect to the estradiol dosage and testosterone dosage calculations in equations 1 through 8 and the corresponding look up tables 1 through 8.

Once the dosage is calculated at process block 606, the system allows the user to decide whether the calculation type (e.g., New Return Booster), is appropriate at decision block 608. If the user deems the calculation type inappropriate at process block 608, the dosage may be recalculated at process block 606. However, if the user deems the calculation type appropriate at process block 608, the user is provided an option to manually adjust the calculation at decision block 610. If the system recognizes that the user does not manually adjust the calculation at decision block 610, the system will prompt the user to prescribe the calculated dosage at process block 612. However, if the system recognizes that the user manually adjusts the calculation at process block 610, the system may record a manually adjusted dosage at process block 614. The system will then prompt the user to prescribe the calculated dosage at process block 612.

Figure 13:
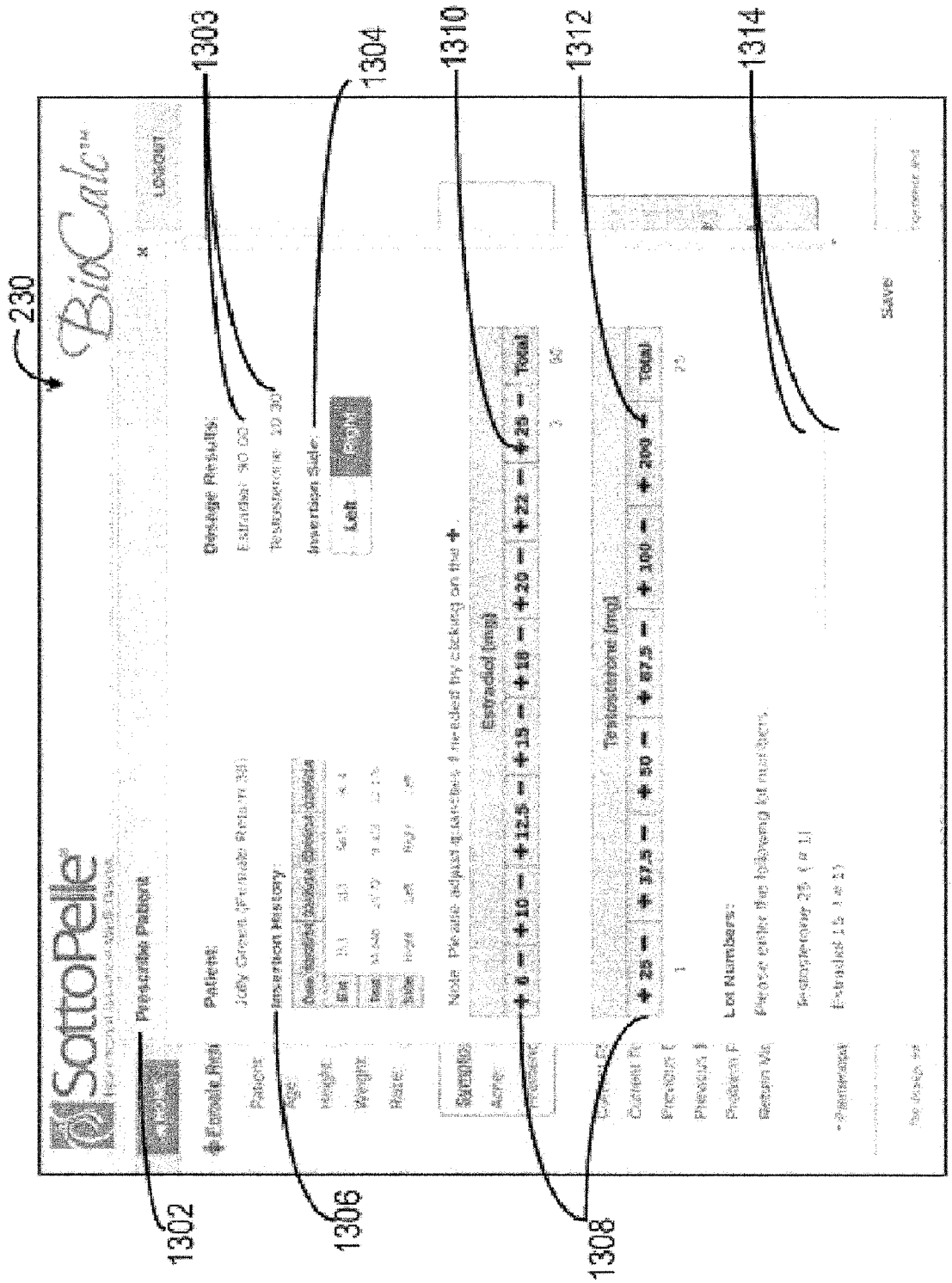
FIG. 13 is an exemplary screen shot of a prescribe patient dialog screen displayed on the user interface.

Referring again to FIG. 12, the system may prompt the user to prescribe the calculated dosage by proving a prescribe button 1222. Clicking the prescribe button 1222 may activate the set of instructions stored on the system controller to display a prescribe patient dialog screen 1302 on the user interface 230, as shown in FIG. 13. The prescribe patient dialog screen 1302 may include calculated dosages 1303, the patient's name, gender and age, and a past insertion history 1306. The patient's past insertion history 1306 may include, for example, the patient's last four insertions, the date of insertion, the estradiol insertion amount in mg, the testosterone insertion amount in mg, the insertion side and the calculation type. As such, the patient's past insertion history 1306 may help support the user's decision making related to a patient's dosages, for example. In one non-limiting example, the patient's past insertion history 1306 may be used to identify an insertion time frame for return dosing for a return or booster patient.

Upon creating the prescription, the system may provide the user with fields on the prescribe patient dialog screen 1302 to enter prescription information. As shown at process block 616 of FIG. 6, the prescription information to be provided may include, but is not limited to, insertion location of the pellet, insertion side, pellet dose, lot numbers and insertion notes about the insertion, all of which may be saved in the patient historical profile.

Insertion location of the pellet may be in the patient's hip or abdomen, for example. Based on the historical insertion information for the patient, the system may default the insertion location value based on the previous insertion, as shown on the prescribe patient dialog screen 1302 in FIG. 13. If the previous insertion location is in the abdomen, for example, the abdomen will be automatically selected. Alternatively, the user may choose to manually change this value. The insertion side 1304 (i.e., left or right) of the pellet may be based on historical insertion information 1306 for the patient. Similar to the insertion location, the system may default the insertion side value based on the previous insertion. For example, if the previous insertion side is on the left, the system will automatically select the opposite side (i.e., the right), as shown in FIG. 13. Alternatively, the user may choose to manually change this value. As such, the system may take the manually entered values corresponding the insertion side and/or location and store them for future dose calculations for the particular patient.

The pellet dose 1308 may be based on the calculated dose, and the system may automatically suggest the combination of pellets that most closely matches the calculated dosage and that yield the least number of pellets, as shown at process block 618 in FIG. 6. As shown in FIG. 13, this is performed for both estradiol and testosterone. The user may manually modify the pellets suggested by the system by clicking on a first icon 1310, such as a plus sign icon, and a second icon 1312, such as a minus sign icon, to increase or decreases the number of pellets, respectively. The system may automatically calculate the pellet dose 1308 based on the pellet sizes chosen and automatically update the pellet dose 1308 totals as the user adds or subtracts pellets. As a non-limiting example, the case where the calculated estradiol dose is 25 mg, the system may suggest two pellets, namely one 15 mg pellet and one 10 mg pellet. However, the user may choose to use two 12.5 mg pellets. Or the user may use his or her discretion to dose a 12.5 mg pellet and a 10 mg pellet using a total of 22.5 mg which is less than the calculated dosage. Whatever the final dosage is selected, the system tracks the actual historical insertion amount.

In another embodiment, the pellet dose 1308 may be automatically calculated at process block 618 in FIG. 6 using a pellet allocation algorithm, for example. The pellet allocation algorithm, as shown in Appendix A, maybe accessed by the set of instructions stored on the system controller to accurately determine optimal pellet insertion given a calculated dosage. Because pellets are in discreet amounts, it is often not possible to insert the exact calculated amount. For example, conventional testosterone pellets are typically available is the following dosages: 25 mg, 37.5 mg, 50 mg, 87.5 mg, 100 mg, and 200 mg. Similarly, conventional estradiol pellets are typically available in the following dosages: 6 mg, 10 mg, 12.5 mg, 15 mg, 18 mg, 20 mg, 22 mg, and 25 mg. In order to calculate the optimal pellet insertion dosage, the pellet allocation algorithm uses the best available approximation, such that the system should produce a final dosage as close to the calculated dosage amount as possible. For instance, if the calculated dosage is 36.75 mg in estradiol, the system may choose a 20 mg+18 mg=38 mg over a sub-optimal allocation of 20 mg+15 mg. There is no bias to the final dosage being greater or less except in the case of the bias being equal, then the system chooses less. The pellet allocation algorithm also uses the least number of pellets to determine the optimal pellet insertion. Since each pellet is an extra subcutaneous insertion, the system targets a pellet combination that minimizes the number of pellets. For example, given a calculated dose of 25 mg estradiol, the system may choose one 25 mg estradiol instead of two 12.5 mg estradiol or one 10 mg and one 15 mg estradiol to achieve the same result. In addition, the pellet allocation algorithm may incorporate some specific biases based on real world experience. For large testosterone doses, a normally suggested single 200 mg is broken into two 100 mg to speed up initial hormone absorption by the body, for example.

The base pellet allocation algorithm, shown in Appendix A, uses a nested loop strategy, such that, for each pellet size starting from the largest to smallest, the pellet size is subtracted from the calculated dose and the result is evaluated. If the result of the subtraction is less than zero then the next smallest pellet size is subtracted from the calculated does and the result is evaluated. If the result of the subtraction is less than zero, then the next (smaller) pellet size is subtracted from the calculated dose. This process is repeated until the result of the subtraction is greater than zero—once greater than zero. If the result of the subtraction is greater than zero, the previous pellet amount result (negative) and the current pellet amount (positive) are compared, and the lesser of the absolute value of the previous pellet amount and the current pellet amount is taken to obtain the closest approximation.

Thus, the pellet allocation algorithm yields a suboptimal approximation in cases where a combination of lesser pellet sizes yields a better approximation when the calculated dose allows for a larger pellet size to be used. For example, if the calculated testosterone is 112.5 mg, based on the base allocation algorithm above, the algorithm would yield one 100 mg testosterone pellet. However, a combination of 87.5 mg+25 mg yields an exact amount. This problem may solved by iterating the base algorithm (above) with the largest pellet being a smaller size with each successive iteration. For instance, the base algorithm would be re-run with the largest testosterone pellet size of 100 mg (sans the 200 mg pellet). If a closer approximation results, then that is taken. If not, the base algorithm is run again with the largest pellet size being the next smallest down. In this instance, the base algorithm is re-run with 87.5 mg being the largest pellet size (sans the 100 mg pellet). On this iteration, the system would arrive at a better approximation than the original run. The iterations would only go on until an exact match is found (in which case there is no longer a need to search for a better approximation) or until the maximum pellet is also the smallest pellet. If a particular iteration yields a solution that is not better than the previous (defined by a smaller absolute value of the difference from the calculated value), then the previous solution is used because it guarantees a lesser number of pellets.

Figure 16:
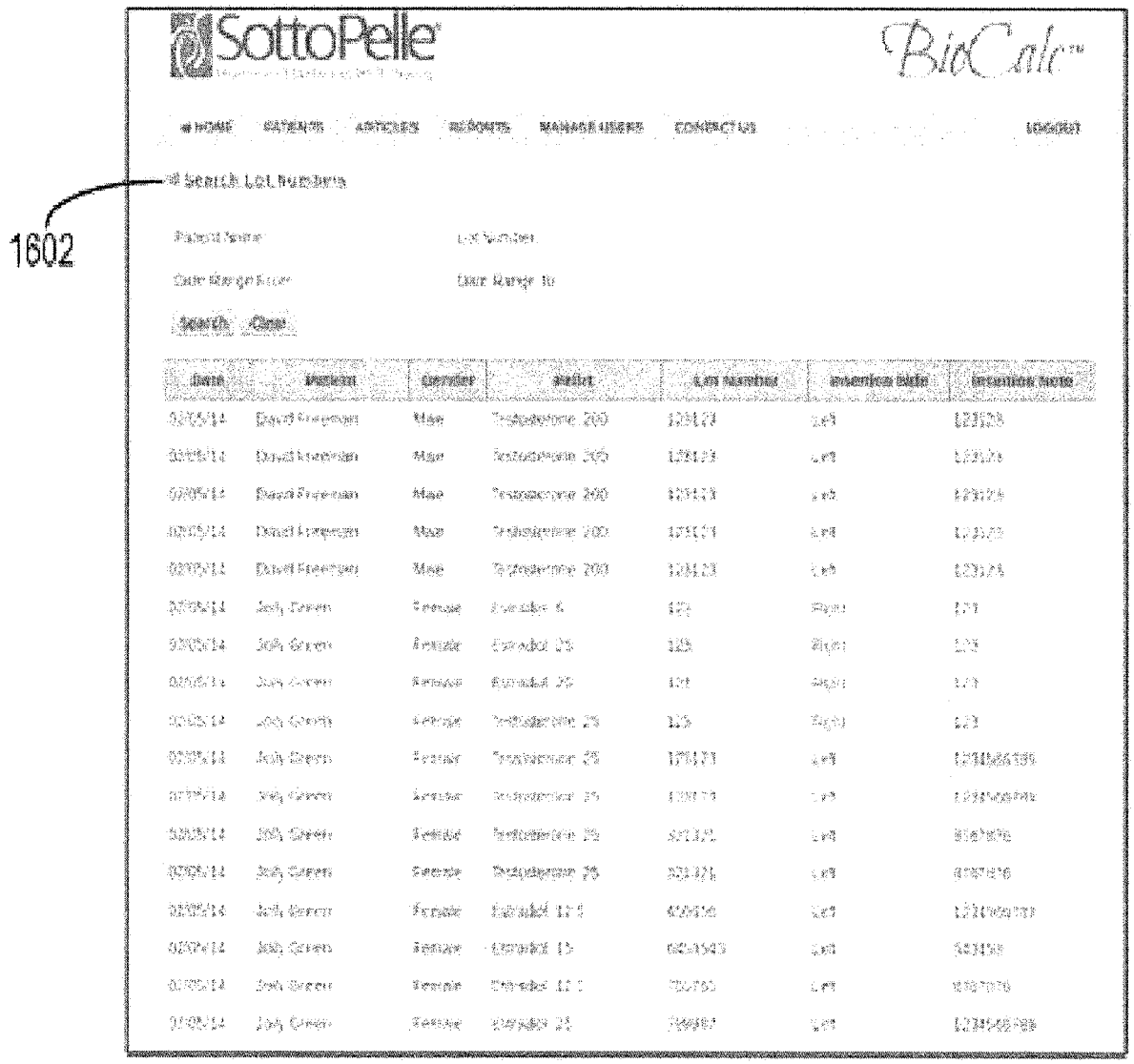
FIG. 16 is an exemplary screen shot of a search screen for searching lot numbers corresponding to the patient.

Once the pellet dose is automatically calculated at process block 618, the user may be provided an option to manually enter the estradiol pellet size insertion and the testosterone pellet size insertion, rather than using the estradiol pellet size insertion and the testosterone pellet size insertion determined by the pellet insertion algorithm. Next, the user may enter the lot numbers corresponding to the pellets to be inserted into the patient at process block 616. Lot number fields 1314, as shown in FIG. 13, may be provided on the prescribe patient dialog screen 1302 for the user to enter the corresponding lot numbers 1501, as shown in FIG. 15. For compliance to health safety rules, all pellets inserted into patients must have the pellet's lot number recorded. Thus, the system creates lot number fields 1314 for each pellet chosen. In the case above, the system would create two lot number fields 1314 to enter the 12.5 mg pellet and the 10 mg pellet. In the case where multiple pellets of the same size are inserted, the system will create lot number fields 1314 for each pellet. For example, if two 12.5 mg pellets are chosen, the system will create two lot number fields. If there are multiple lot number fields of the same pellet type and size, a copy icon 1502, as shown in FIG. 15, can copy the lot number of the pellet above. It is often the case that the similar type and size pellets carry the same lot number. In addition, once lot numbers are entered into the system, the user may use a search lot numbers function 1602, as shown in FIG. 16, to find lot numbers by patient name, lot number, and insertion date range, for example.

Once the insertion location of the pellet, insertion side, pellet dose, lot numbers and insertion notes about the insertion are obtained at process block 616 in FIG. 6, another user, for example a medical assistant, may adjust the patient information and enter new patient information, such at a blood work number, at process block 620. Each time a patient returns for additional dosages, the steps 600 are repeated for the existing patient and saved in the patient's profile for future dosage calculations.

In yet another embodiment, the dosage system may consider the number of return visits when factoring the calculated dosing value. For example, upon the first return of a female dosing patient, the testosterone dosage amount may be reduced by 12.5 mg prior to taking into account historical factors. Previously, the return calculation for females was driven by the previous testosterone dose multiplied by historical factors. The historical factors being, but not limited to, acne, facial Hair, and history of PCOS. The new calculation is as follows in Equation (9):

Testosterone dosage=(previous testosterone dose−12.5)*historical factors

Figure 14:
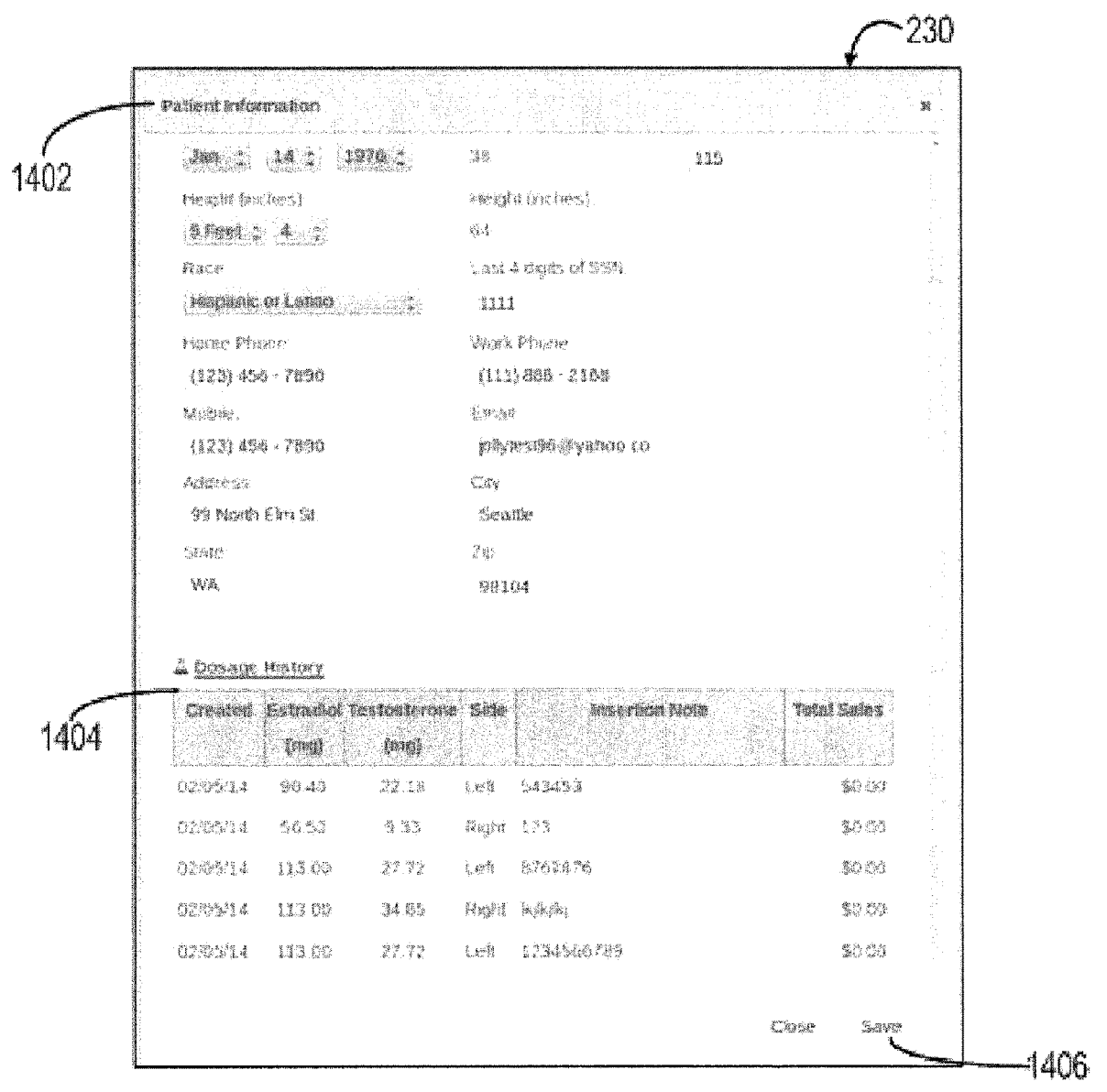

As shown in FIG. 14, a patient information dialog screen 1402 is shown on the user interface 230 of the communication device. The patient information dialog screen 1402 may display the patient's insertion history 1404. In the embodiment shown in FIG. 14, when the user clicks on the new patient button 910 of FIG. 9, the patient information dialog screen 1402 is displayed on the user interface 230. The patient information can be modified by the user prior to clicking the save button 1406.

In addition to the factors used to calculate the dosage in equation (9) above, non-pellet testosterone usage may be incorporated. For example, if non-pellet testosterone is indicated in the calculation, then testosterone calculation is set to 0.00. In addition, or alternatively, if a return patient is premenopausal and their current estradiol level is greater than 10 mg, for example, and the patient does not show symptoms of menstrual migraines, then the estradiol return and booster calculation is set to 0.00. Physical activity level may also be incorporated into the dosage calculation. The physical activity level of the patient may include, but is not limited to, sedentary/work only, work plus exercise three times per week, and work plus exercise five time per week. If the activity level of the patient is indicated as sedentary/work only, the dosage calculation may be configured to decrease the testosterone dose by 100.00 mg, for example. If the activity level of the patient is indicated as work plus exercise three times per week or work plus exercise five time per week, the dosage calculation may be configured to increase the testosterone dose by an appropriate mg and 100.00 mg, respectively. In addition, if the patient has a history of BPH, the dosage calculation may be configured to decrease the testosterone calculation by 5%, for example. Alternatively, if the patient has a history of prostate cancer, the dosage calculation may be configured to decrease the testosterone calculation by 5%. Or if the patient has a history of both BPH and prostate cancer, the dosage calculation may be configured to decrease the testosterone calculation by 10%, for example.

In one exemplary embodiment, the above described dosing system may include a comprehensive toolkit for providing hormone replacement therapy. The comprehensive toolkit may provide ancillary support functions, including, but not limited to, patient consult requests and response, articles, videos, forms, news and updates, products purchasing, financial reports, and assistant assignments.

The patient consult function may allow users to submit a question for a particular patient, for example. To begin a patient consult, the system may securely route the consult request electronically to Sottopelle Therapy headquarters, for example. A notification email may then be sent alerting staff of the HRT provider and the consult request can be pulled from a database application. A response can be written into the consult request record, and a notification email may be sent to the provider requesting the consult that their consult request has been responded to. The user can go to a patient consults area where they can securely view past and present patient consults.

Figure 17:
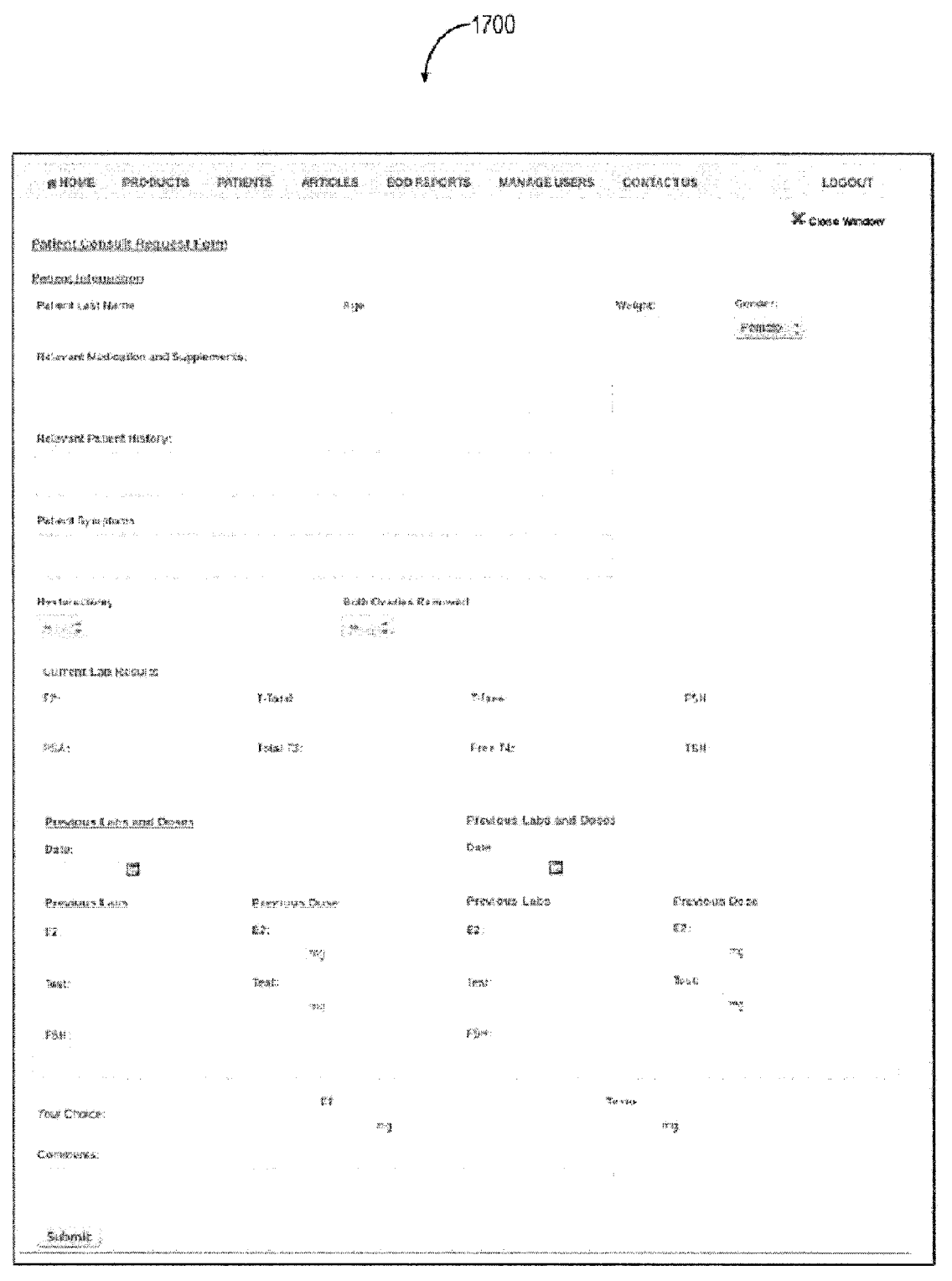

Users can initiate a patient consult request by filling out information about the patient using a form 1700, as shown in FIG. 17. The system will automatically fill in patient information based on the patient selected. The following fields are available to describe the patient's situation: patient last name, age, weight, gender, relevant medication and supplements, relevant patient history, patient symptoms, hysterectomy, both ovaries removed, lab results label, E2, T-total, PSA, T-free, total T3, free T4, FSH, TSH, previous labs and dosages, date, previous labs:E2, previous dosage: E2, previous labs: test, previous dosage: test, previous labs: FSH, date, previous labs:E2, previous labs: test, previous dosage:E2, previous dosage: test, previous labs: FSH, your choice, your choice:E2, your choice: test. Once the form 1700 is submitted, the provider is notified via email and the patient consult request record becomes visible in the patient consult response application.

Figure 18:
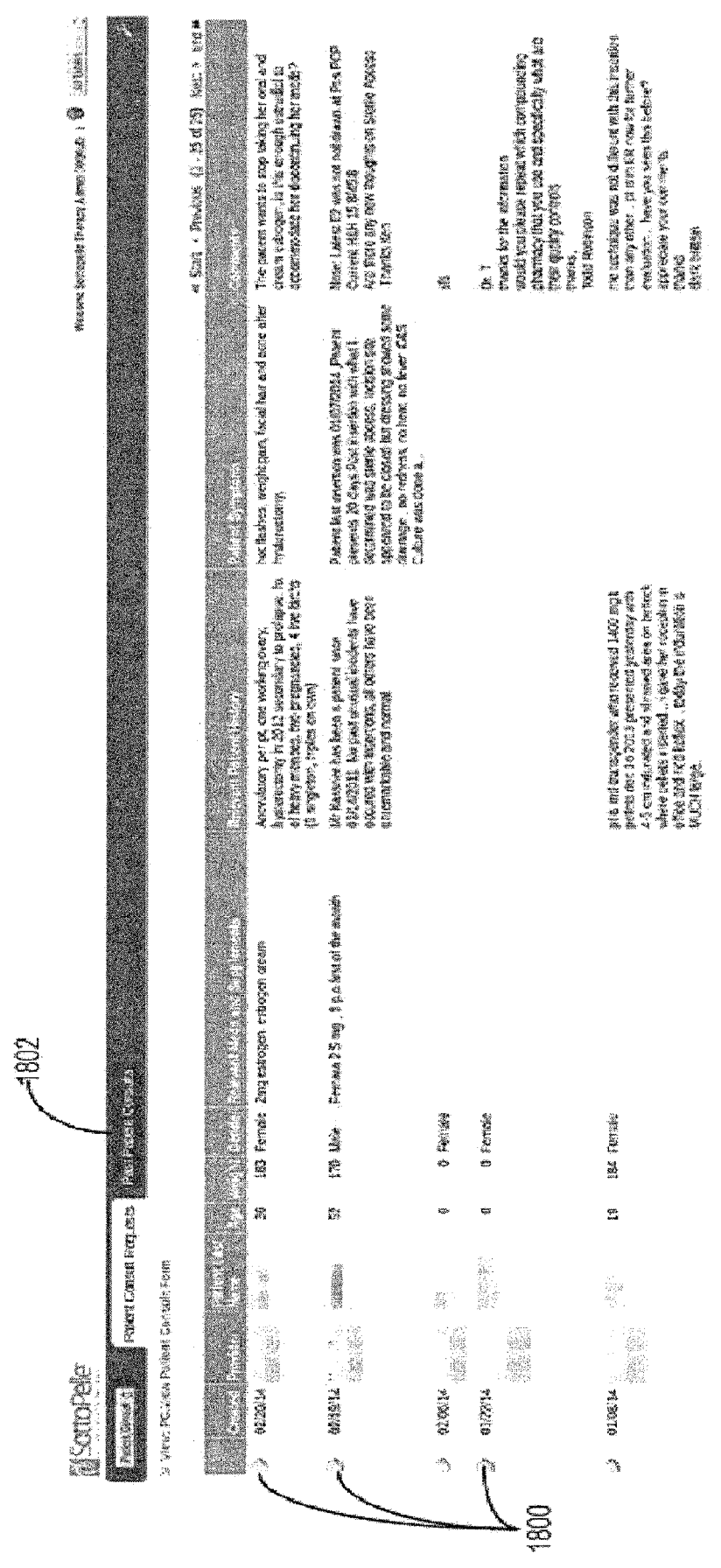
Figure 19:
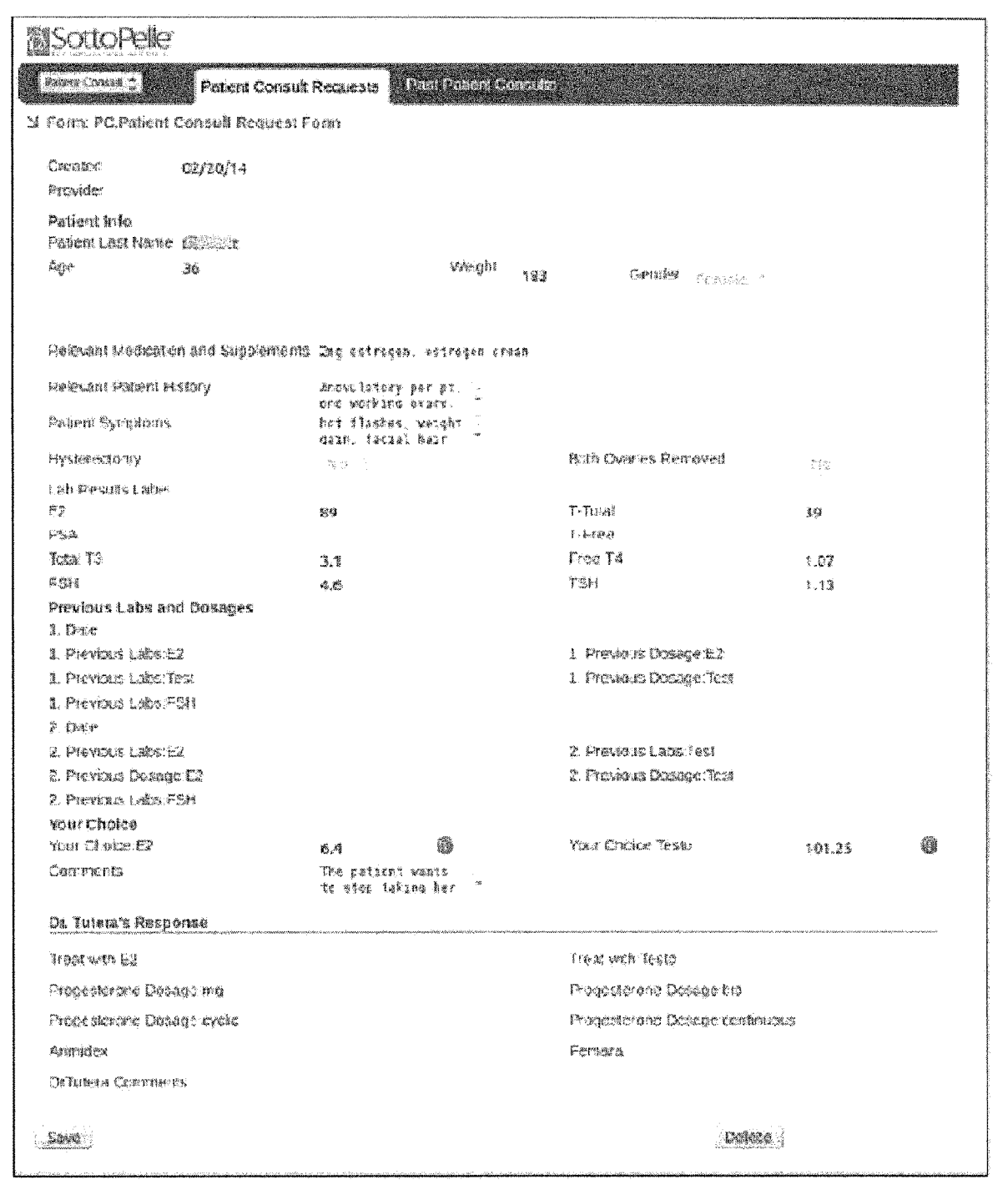
Figure 20:
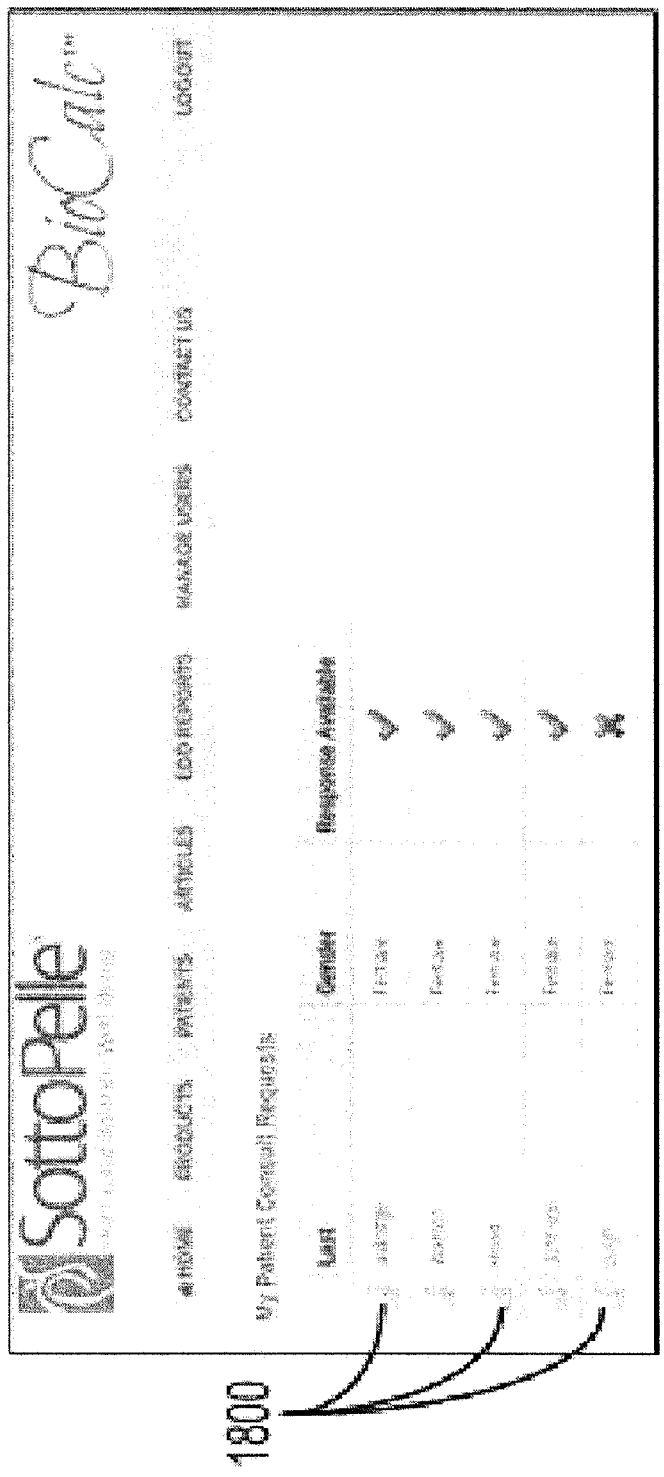
FIG. 20 is an exemplary screen shot of a patient consult requests status screen.
Figure 21:
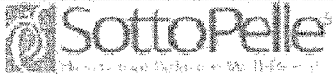
FIG. 21 is an exemplary screen shot of a patient consult response screen showing relevant patient parameters and a recommended course of action.

The system may display consult requests 1800 awaiting response, as shown in FIG. 18, as well as a tab 1802 for past patient consults, to allow users to edit the patient consult records and submit a response. Users may respond to a patient consult with some or all patient consult information conveniently visible, as shown in FIG. 19. Once a response is submitted, the provider is notified via email and the patient consult response record becomes visible in the patient consult response application. Users may also be provided with the status of the patient consult requests 1800, as shown in FIG. 20, indicating if the response is available or unavailable, for example. The patient consult concludes with a printable page of all relevant parameters along with a response to the particular patient's condition and recommended course of action, as shown in FIG. 21.

Figure 23:
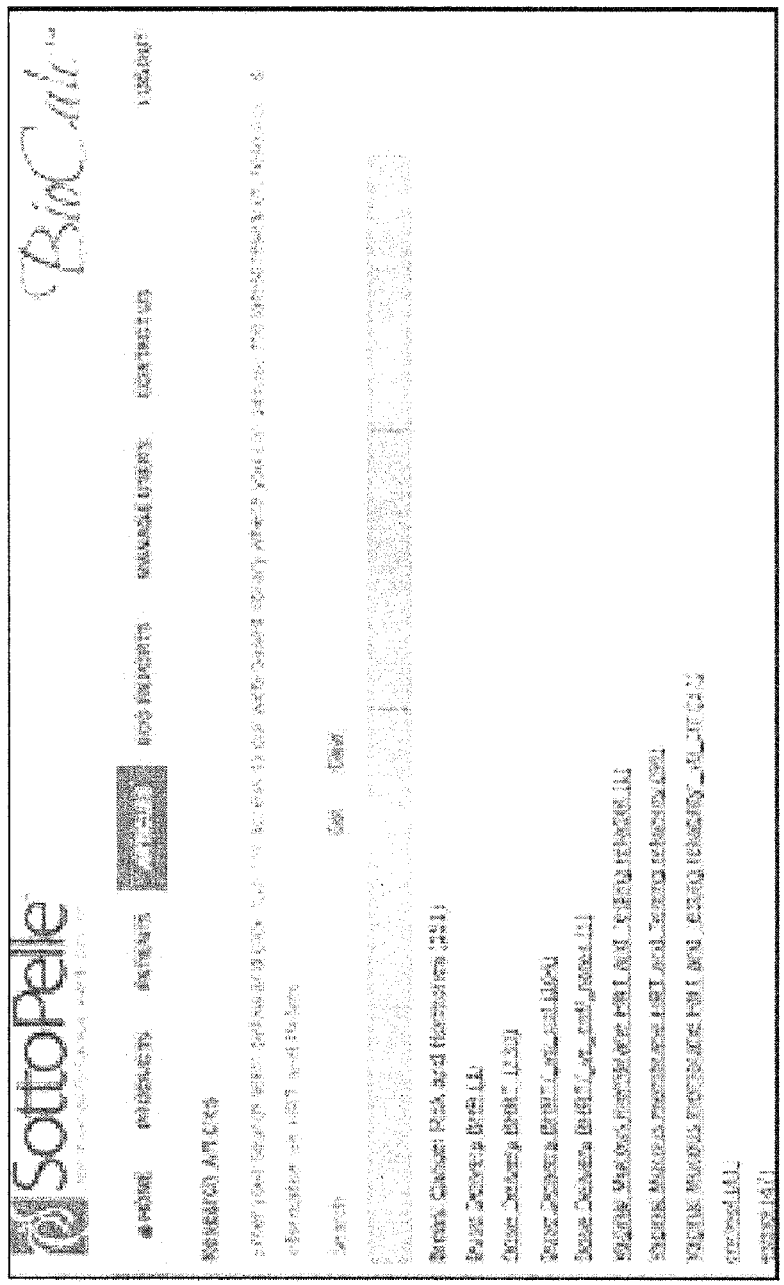
FIG. 23 is an exemplary screen shot of a knowledge base articles search screen for searching through relevant articles on hormone replacement therapy.

In one embodiment, the system offers informational resources pertaining to hormone replacement therapy articles, videos, forms, news and updates, as shown in FIG. 22. News videos and updates may include, but are not limited to Instagram videos, Twitter texts, Facebook posts, Pinterest photos, Sottopelle and Hormone Replacement Therapy News, marketing brochures, office forms, important articles, and instructional videos. As shown in FIG. 23, users may also search through relevant articles on hormone replacement therapy by entering a search term. The system can then access the web-based library to obtain the latest research, resources and information on HRT and pellets. Further, as shown in FIG. 24, the system allows for the following products to be purchased including, but not limited to, hair repair, DIM, health and wellness, oil of evening primrose, calcium pyruvate, liquid vitamin D3, traumeel tablets, sleep wellness, slow flow, TrocarPak female, TrocarPak male, male trochar kit, and female trochar kit.

Figure 25:
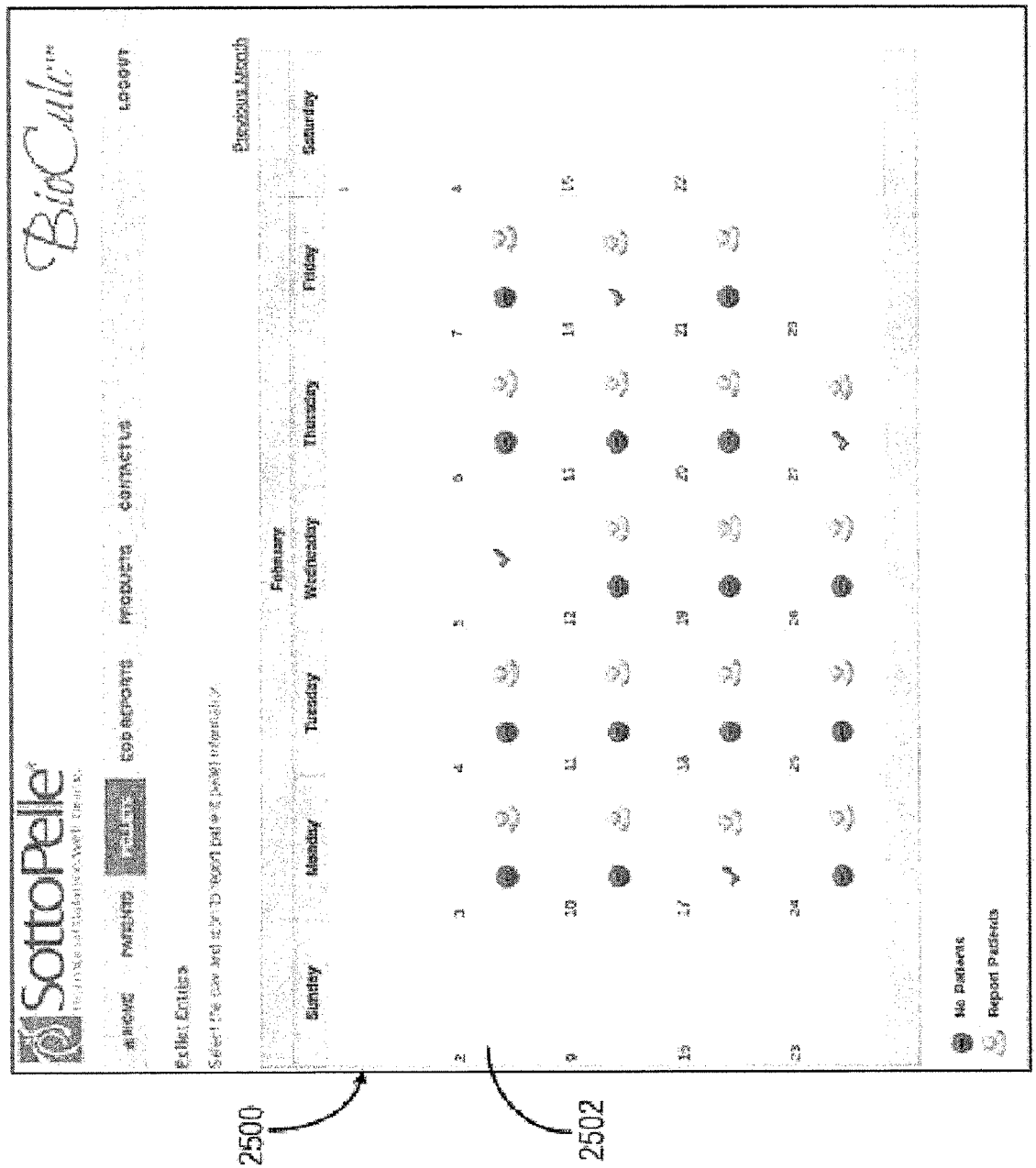
FIG. 25 is an exemplary screen shot of a pellet calendar for assigning financial numbers to patient prescriptions.
Figure 26:
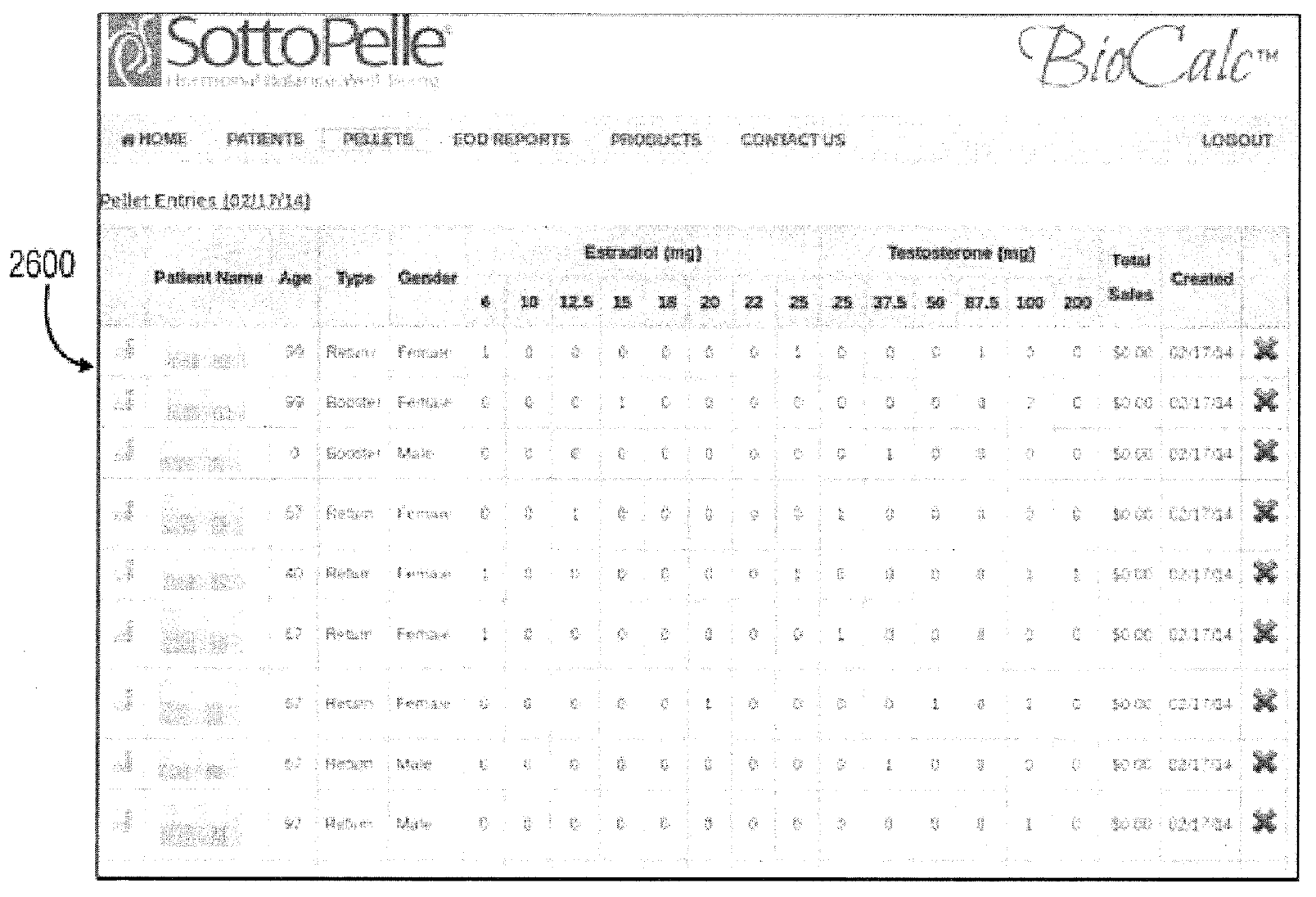
Figure 27:
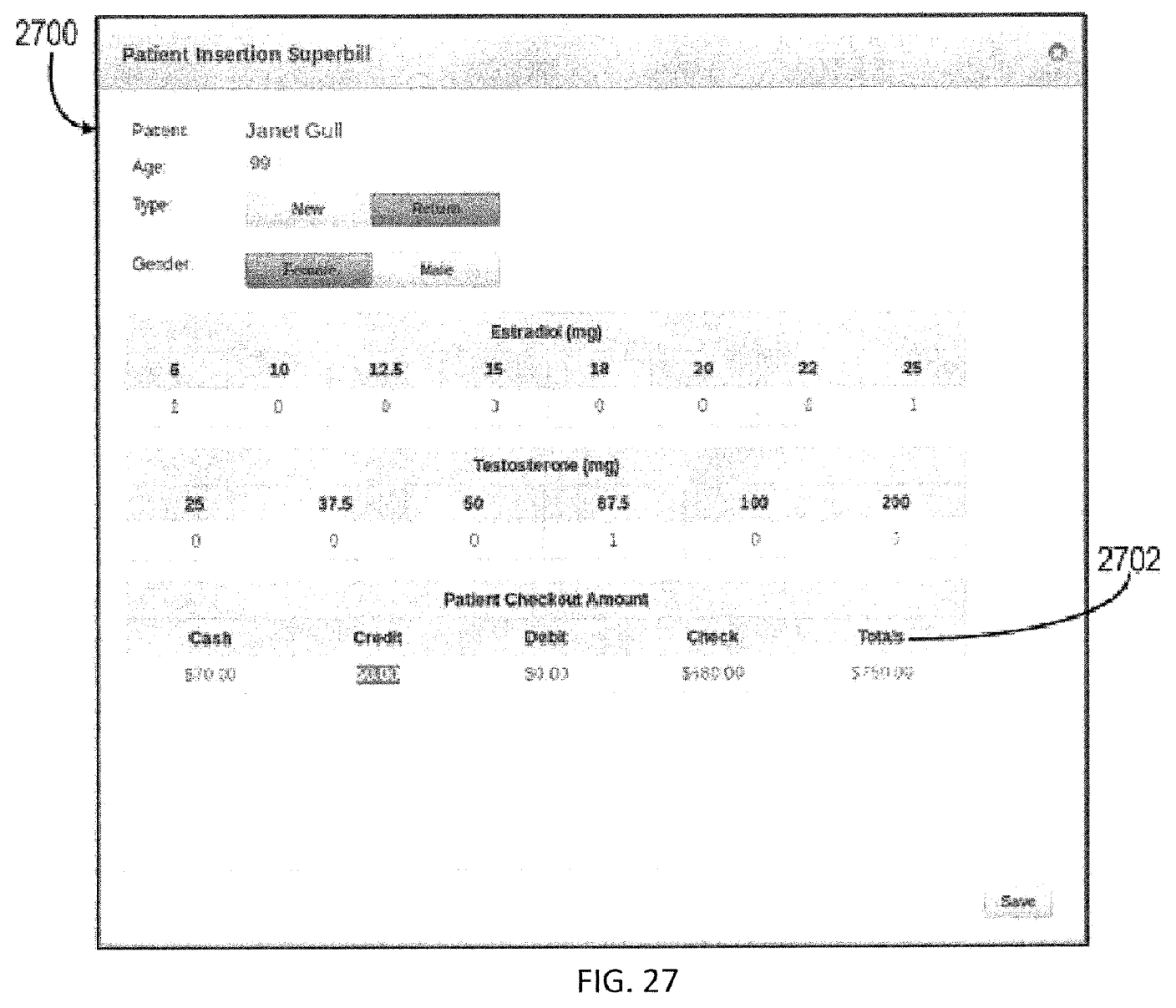

The dosing system may also provide tools for tracking revenues per patient visit. By doing so, the system can generate end-of-day top line reports on a per office level to providers needing to get a clearer financial picture of their practice. The system can automatically populate a pellet calendar 2500, shown in FIG. 25, with patient prescriptions as described previously. Medical assistants, for example, as well as providers can view the pellet calendar 2500 which allows for financial numbers to be assigned to each prescription. Users can do this by clicking on a day 2502. The system automatically populates a daily pellet list 2600, as shown in FIG. 26, allowing users to enter financial information attached to each visit. The daily pellet list 2600 may show, but is not limited to, the following values: patient name, age, visit type (new/return/booster), gender (male/female), estradiol pellets inserted during the visit, and testosterone pellets inserted during the visit In another embodiment, the system provides a patient insertion superbill modal window 2700, shown in FIG. 27, that allows for patient checkout amounts to be attached to each patient visit. The patient information and pellet insertion amounts may all automatically be pre-filled and include: patient name, age, visit type (new/return/booster), gender (male/female), estradiol pellets inserted during the visit, and testosterone pellets inserted during the visit. Thus, the users can enter financial information (e.g., cash, credit, debit, check) into the superbill modal window 2700 and totals 2702 can be automatically calculated.

Figure 28:
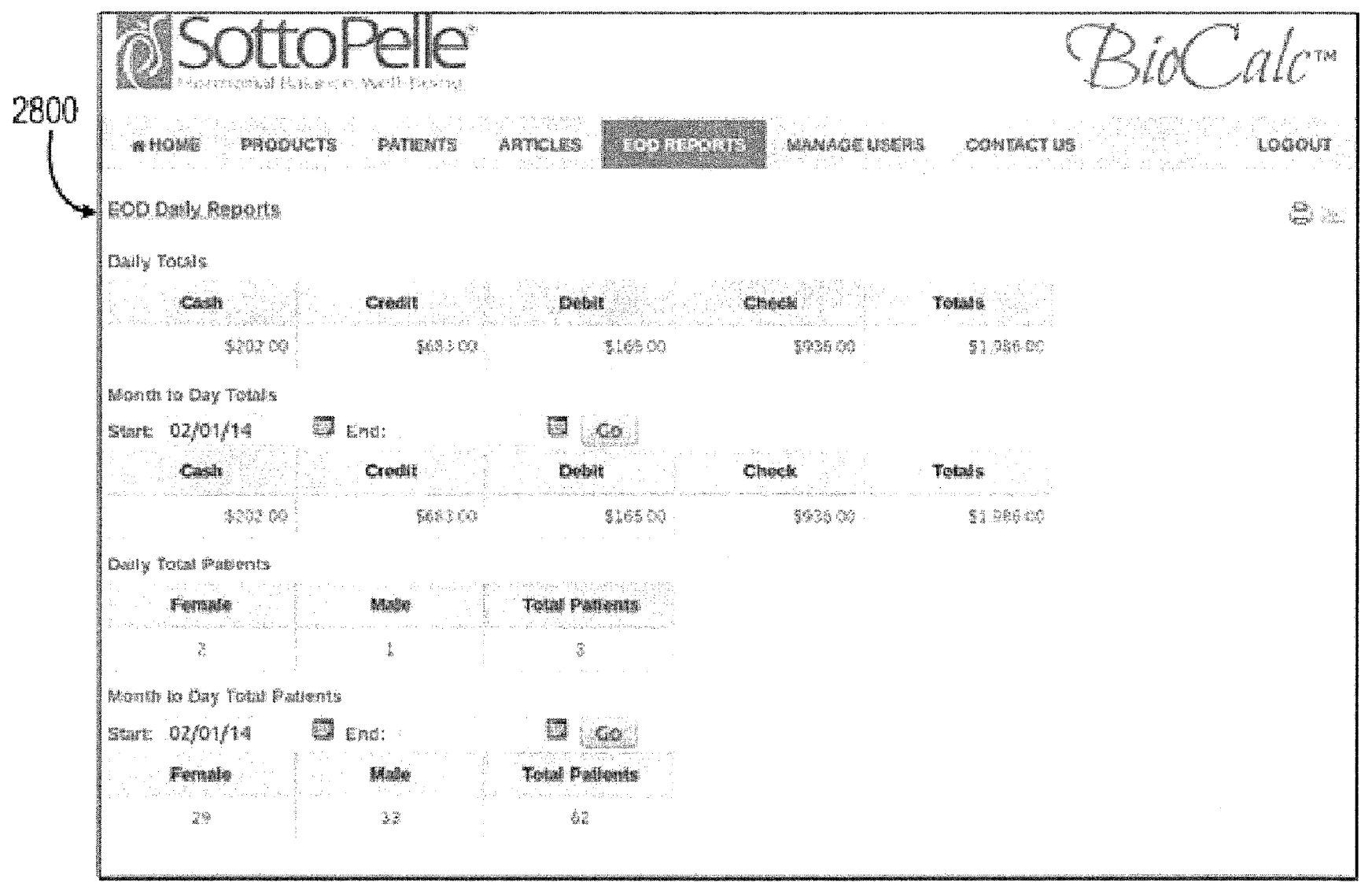

The financial information and patient visits can be summarized to provide a full financial view of the practice in the form of an end of day (EOD) report 2800, as shown in FIG. 28. The following metrics may automatically be calculated and displayed in a format that can be printed and emailed: (1) Daily totals: cash, credit, debit, check and grand total; (2) Month To Day Totals: cash, credit, debit, check and grand total—includes a date range search; (3) Daily Total Patient: count patients for the day for each gender; and (4) Month to Day Total Patients: count patients for the day for each gender and may includes a date range search.

The financial numbers may be aggregated for the provider to track the number of patients, prescription and pellets to manage day-to-day operations including patient and gender count per provider for a given date range, revenues per provider for a given date range, and dosing fee per provider for a given date range. The financial numbers may be displayed in the form of a prescription summary report 2900, for example, as shown in FIG. 29.

Figure 30:
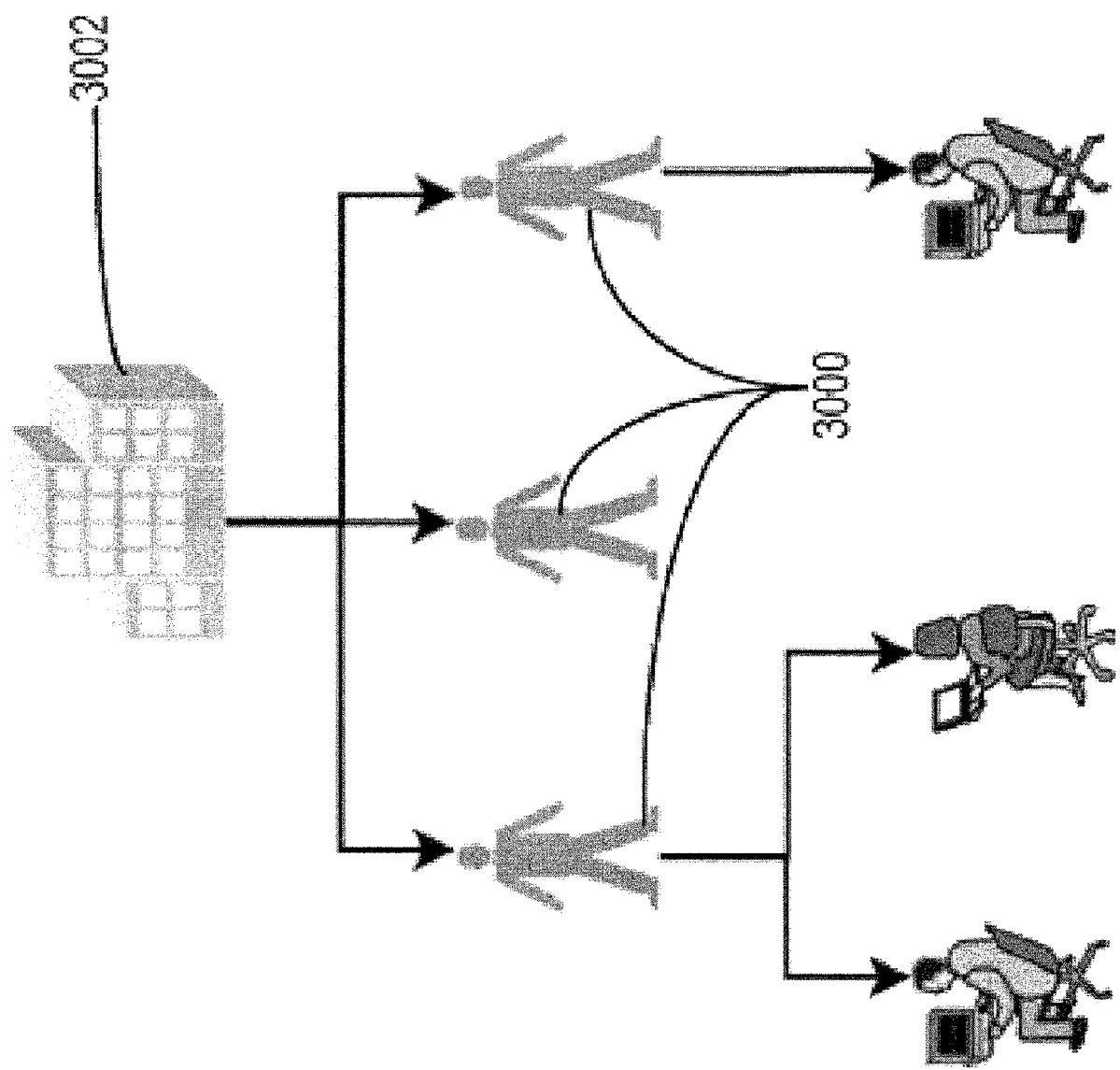
FIG. 30 is a schematic diagram of an organization structure configured to be implemented into the system of FIG. 1.
Figure 31:
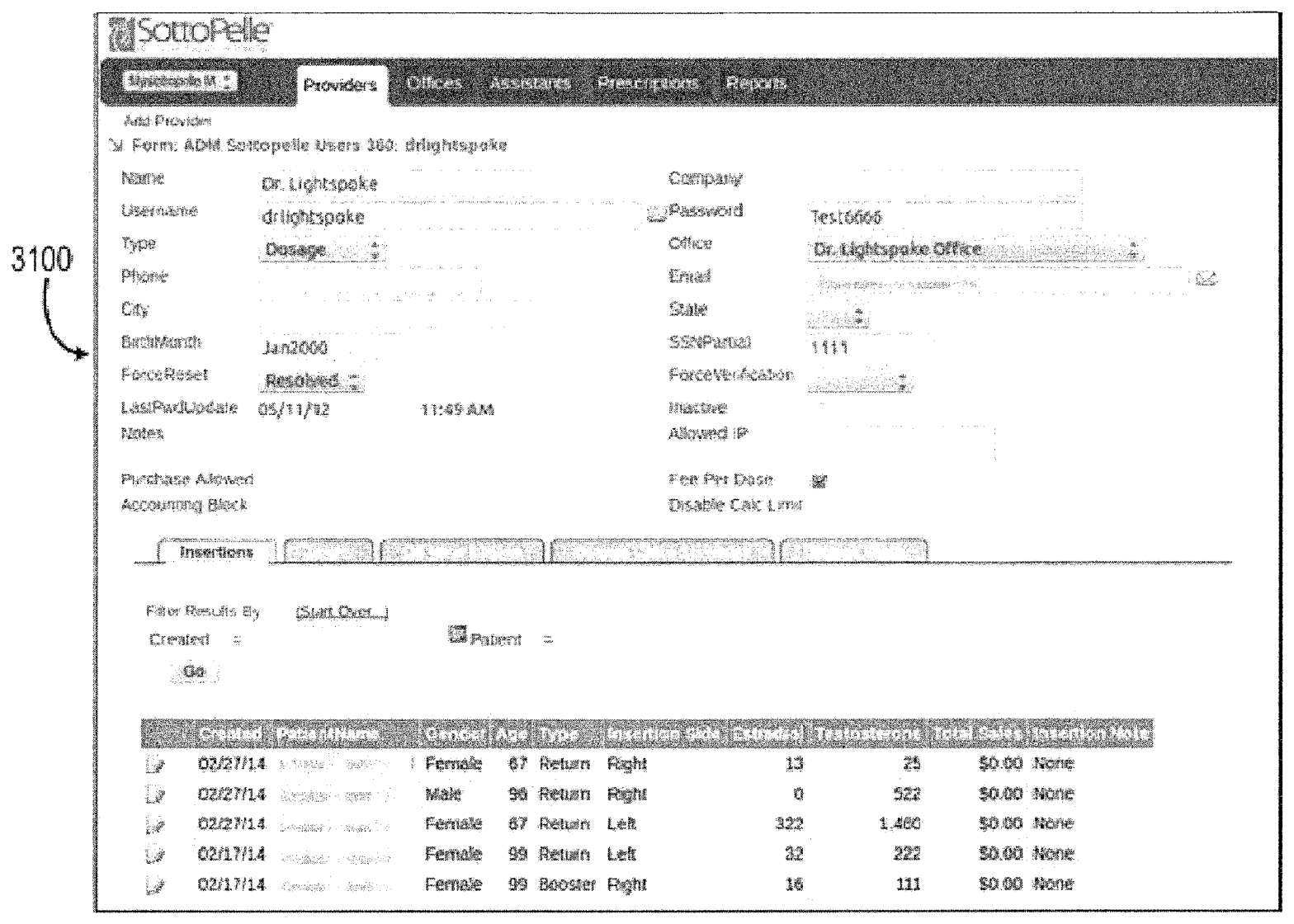
Figure 32:
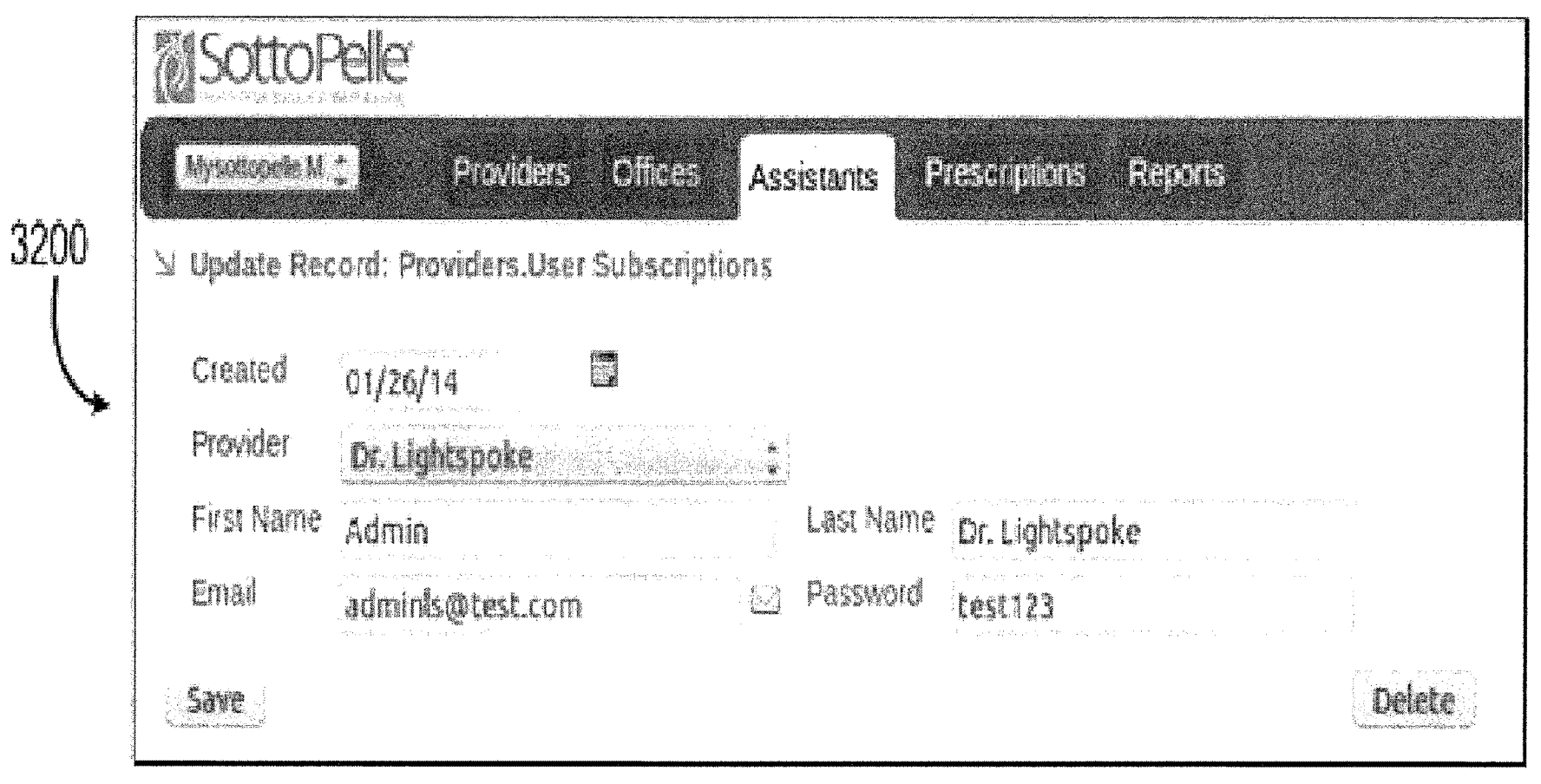

The system may be a full multi-user system allowing providers to create secure login for assistants, for example, to interact with patients, pellet insertions, and other patient visit information. The system automatically keeps track of which login belongs to which provider so when the assistant logs in, only patients related to the corresponding office are shown. Multiple providers 3000 can be linked to the same office 3002, as shown in FIG. 30, allowing multiple providers in the same office to share patient information, and allowing a provider record 3100 to specify an office, as shown in FIG. 31. Likewise, a medical assistant login 3200 may be linked to a provider, as shown in FIG. 32.

The present invention has been described in terms of one or more preferred embodiments, and it should be appreciated that many equivalents, alternatives, variations, and modifications, aside from those expressly stated, are possible and within the scope of the invention.

I claim:

1. A computer-implemented method for hormone replacement therapy comprising:

receiving, by a computerized device comprising a processor, an input device, and a display screen, a patient identifier;

retrieving, by the processor, a patient record that corresponds to the patient identifier;

determining, by the processor, a patient status as one of a returning patient and a booster patient;

determining by the processor at least one of an effective estradiol dosage and an effective testosterone dosage using at least one dosage calculation method selected based on the patient status, a patient gender from the retrieved patient record, one or more automated gender-specific input parameters, and one or more gender-specific tracking parameters;

displaying, on the display screen, the at least one determined effective dosage;

administering a pellet comprising the at least one determined effective dosage to the patient;

displaying, by the display screen, at least one of an estradiol pellet size insertion and a testosterone pellet size insertion corresponding to the at least one of the effective estradiol dosage and the effective testosterone dosage;

receiving, by the input device, at least one of an increase and a decrease in the at least one of the estradiol pellet size insertion and the testosterone pellet size insertion; and calculating, by the processor, at least one of an updated effective estradiol dosage and an updated effective testosterone dosage based on the input signal of the user.

2. The method of claim 1, wherein the one or more automated gender-specific input parameters is stored in the retrieved patient record and comprises at least one of a physical activity level, a quantity of patient visits, a patient age, a patient height, a patient weight, a patient race, a number of pregnancies, a number of live births, a number of abortions, a history of renal disease, a history of active liver disease, a hysterectomy, a history of cervical cancer, a history of ovarian cancer, a history of fibrocystic breast disease, a history of breast cancer, a current follicle stimulating hormone (FSH) level, a current testosterone level, a current estradiol level, a current non-pellet estradiol dose, a current non-pellet testosterone dose, a history of acne, a history of facial hair, a history of hair loss, a history of prostate cancer, a history of polycystic ovary syndrome (PCOS), a history of hysterectomy, a history of heavy menses, and a history of metabolic syndrome.

3. The method of claim 2, further comprising automatically calculating, by the processor, at least one of the patient age based on a date of birth from the retrieved patient record.

4. The method of claim 2, wherein when the patient sex is female, the method further comprises:
receiving, by the processor, female non-pellet testosterone usage of the patient, a pre-menopausal or post-menopausal patient status, an estradiol level of the patient, and a migraine status of the patient;
determining, by the processor, an estradiol dosage=0 in response to receiving an estradiol level of the patient that is greater than 10 milligrams and a migraine status of the patient that indicates that the patient has migraines; and
determining, by the processor, a testosterone dosage=0 in response to receiving a female non-pellet testosterone usage of the patent that is greater than zero milligrams.

5. The method of claim 1, further comprising displaying the previous insertion date, the previous testosterone dose, the previous estradiol dose, the pellet insertion location, and the pellet insertion side from the retrieved patient record on the display screen for the user at a time of insertion.

6. The method of claim 1, further comprising determining, by the processor, a new pellet insertion location based on at least one of the pellet insertion location, the previous insertion date, the previous testosterone dose and the previous estradiol dose from the retrieved patient record.

7. The method of claim 1, wherein using the at least one dosage calculation method comprises tracking at least one of a pellet insertion location, a pellet insertion side, a pellet dose, a pellet lot number, an insertion note, a previous testosterone dose, and a previous estradiol dose.

8. The method of claim 7, wherein the tracking comprises storing the at least one of the pellet insertion location, the pellet insertion side, the pellet dose, the pellet lot number, the insertion note, the previous testosterone dose, and the previous estradiol dose in the patient record.

9. The method of claim 6, wherein tracking the pellet insertion location and the pellet insertion side is based on historical insertion information including at least one of a hip location, an abdominal location, a left side, and a right side; and wherein, based on the historical insertion information, the pellet insertion location and the pellet insertion side are determined by the processor.

10. The method of claim 9, further comprising receiving a user input of the at least one of the pellet insertion location and the pellet insertion side, the at least one of the pellet insertion location and the pellet insertion side being different from the pellet insertion location and the pellet insertion side determined by the processor.

11. The method of claim 8, wherein tracking the pellet lot number comprises entering one or more corresponding lot numbers into at least one lot number field provided on the display screen of the input device and storing the entered at least one lot number in the patient record.

12. The method of claim 1, further comprising determining by the processor at least one of an estradiol pellet size insertion and a testosterone pellet size insertion corresponding to the at least one of the effective estradiol dosage and the effective testosterone dosage using a pellet allocation algorithm, wherein a quantity of the at least one of the estradiol pellet size insertion and the testosterone pellet size insertion is minimized.

13. The method of claim 12, further comprising receiving a user input of at least one of the estradiol pellet size insertion and the testosterone pellet size insertion, the at least one of the estradiol pellet size insertion and the testosterone pellet size insertion being different from the estradiol pellet size insertion and the testosterone pellet size insertion determined by the processor.

14. The method of claim 12, further comprising:
ordering, by the processor, a plurality of pellet sizes from largest to smallest;
subtracting, by the processor, a largest of the plurality of pellet sizes from the effective dosage; and
if a result of the subtraction is greater than zero, assigning, by the processor, the largest of the plurality of pellet sizes as the estradiol pellet size insertion or the testosterone pellet size insertion;
if a result of the subtraction is less than zero, subtracting, by the processor, a next smallest one of the plurality of pellet sizes from the effective dosage until the result is greater than zero;
calculating, by the processor, an absolute value of the result of the subtraction that is less than zero and an absolute value of the result of the subtraction that is greater than zero; and
assigning, by the processor, one of the plurality of pellet sizes as the estradiol pellet size insertion or the testosterone pellet size insertion corresponding to the result having a lesser absolute value.

15. The method of claim 1, further comprising displaying, from the retrieved patient record, a past insertion history on the display screen corresponding to the patient, wherein the past insertion history includes at least one of a previous insertion date, a previous testosterone dose, a previous estradiol dose, a pellet insertion location, and a pellet insertion side.

16. The method of claim 15, further comprising identifying, using the past insertion history, an insertion time frame for return dosing for at least one of the returning patient and the booster patient.

* * * * *